(12) United States Patent
Tsuchida

(10) Patent No.: US 8,450,417 B2
(45) Date of Patent: May 28, 2013

(54) ORGANOSILICON COMPOUNDS, PRODUCTION PROCESSES THEREOF, PRESSURE-SENSITIVE ADHESIVE COMPOSITIONS CONTAINING THE ORGANOSILICON COMPOUNDS, SELF-ADHESIVE POLARIZERS AND LIQUID CRYSTAL DISPLAYS

(75) Inventor: Kazuhiro Tsuchida, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/598,909

(22) Filed: Aug. 30, 2012

(65) Prior Publication Data

US 2012/0322946 A1      Dec. 20, 2012

Related U.S. Application Data

(62) Division of application No. 12/553,601, filed on Sep. 3, 2009, now abandoned.

(30) Foreign Application Priority Data

Sep. 5, 2008  (JP) ................................ 2008-227777

(51) Int. Cl.
*C08F 8/00* (2006.01)
(52) U.S. Cl.
USPC ............................................ 525/100; 546/14
(58) Field of Classification Search
USPC ........................................... 525/100; 546/14
See application file for complete search history.

(56) References Cited

U.S. PATENT DOCUMENTS

| 3,071,561 A | 1/1963 | Bluestein |
| 5,194,555 A | 3/1993 | Zeldin et al. |
| 7,169,949 B2 | 1/2007 | Boisseau et al. |
| 7,309,737 B2 * | 12/2007 | Kim et al. .................... 525/100 |

FOREIGN PATENT DOCUMENTS

| JP | 8-104855 A | 4/1996 |
| JP | 8-199144 A | 8/1996 |
| JP | 3022993 B2 | 3/2000 |
| JP | 2007-131556 A | 5/2007 |
| JP | 2008-506028 A | 2/2008 |

OTHER PUBLICATIONS

E. Jin Cho et al.,; "A mesoporous silica functionalized by a covalently bound pyridine derivative for selective optical sensing of thymidine"; Materials Letters, 2007, 61, pp. 5157-5160.

Japanese Office Action dated Oct. 20, 2010, issued in corresponding Japanese Patent Application No. 2008-227777.
Q. M. Wang et al., "Molecular assembly of red and green nanophosphors from amine-functionalized covalent linking hybrids with emitting center center of Eu3+ and Tb3+ ions"; Journal of Photochemistry and Photobiology A: Chemistry, 2006, 178, pp. 70-75.

* cited by examiner

*Primary Examiner* — Margaret Moore
(74) *Attorney, Agent, or Firm* — Westerman, Hattori, Daniels & Adrian, LLP

(57) ABSTRACT

Organosilicon compounds are represented by the following formula:

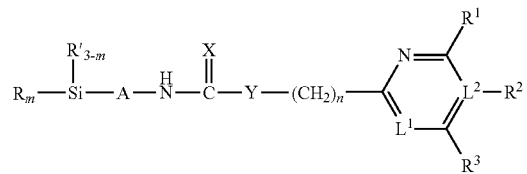

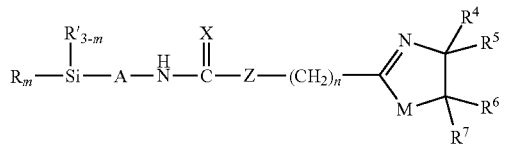

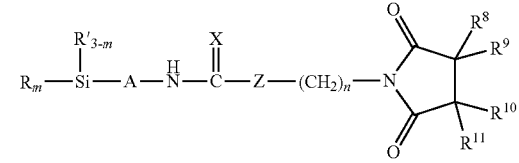

wherein R is a hydrolyzable group, R' is an alkyl having 1 to 4 carbon atoms, A is an alkylene having 1 to 6 carbon atoms, X is O or S, Y is —NH— or S, $L^1$ and $L^2$ are C or N, Z and M are —NH—, O or S, $R^1$ to $R^{11}$ are H, alkyl having 1 to 6 carbon atoms, alkoxy or fluoroalkyl, or amino, m is 1 to 3, and n is 0 to 3. $R^1$ and $R^2$ or $R^2$ and $R^3$ may bonded together. $R^5$ and $R^6$ or $R^9$ and $R^{10}$ may directly bond together. $R^4$ and $R^7$ or $R^8$ and $R^{11}$ may form a ring skeleton. Their production processes, pressure-sensitive adhesive compositions, self-adhesive polarizers and LCDs are also disclosed.

5 Claims, 5 Drawing Sheets

ORGANOSILICON COMPOUNDS, PRODUCTION PROCESSES THEREOF, PRESSURE-SENSITIVE ADHESIVE COMPOSITIONS CONTAINING THE ORGANOSILICON COMPOUNDS, SELF-ADHESIVE POLARIZERS AND LIQUID CRYSTAL DISPLAYS

CROSS-REFERENCE TO RELATED APPLICATIONS

This application is a divisional application of U.S. application Ser. No. 12/553,601, filed Sep. 3, 2009 now abandoned, in which this non-provisional application is based upon and claims priority under 35 U.S.C. §119(a) on Japanese Patent Application No. 2008-227777, filed Sep. 5, 2008, the entire contents of which are incorporated herein by reference.

TECHNICAL FIELD

This invention relates to organosilicon compounds, and more specifically to organosilicon compounds capable of producing excellent bonding force with hydroxyl-containing matrix resins owing to the inclusion of two or more functional groups having coordination property with active hydrogen atoms in hydroxyl groups or the like and hence, significantly improving the adhesion and rework capability between pressure-sensitive adhesives containing the matrix resins and base materials. The present invention is also concerned with their production processes, pressure-sensitive adhesive compositions containing the organosilicon compounds, self-adhesive polarizers having pressure-sensitive adhesive layers formed from the pressure-sensitive adhesive compositions, and liquid crystal displays including the self-adhesive polarizers.

BACKGROUND ART

A silane coupling agent has two or more different functional groups in its molecule, and acts as a mediator for joining an organic material and an inorganic material together although such organic and inorganic materials can be hardly joined together in general. One of the functional groups is a hydrolyzable silyl group, and in the presence of water, forms a silanol group. As a result of a reaction with a hydroxyl group on the surface of an inorganic material, the silanol group forms a chemical bond with the surface of the inorganic material. The other or another functional group is an organic reactive group such as a vinyl, epoxy, amino, (meth)acryl or mercapto group, which forms a chemical bond with an organic material such as a synthetic resin. Making use of these properties, silane coupling agents are widely used as modifiers for organic and inorganic resins, adhesion aids, various additives and the like.

Among such applications of silane coupling agents, their application as pressure-sensitive adhesives is representative. For pressure-sensitive adhesives to be used upon bonding liquid crystal cells and optical films together, for example, there is an outstanding demand for still higher adhesion performance as a result of the move toward greater and wider liquid crystal displays (LCD).

In the case of LCDs, there is an ever-increasing move toward larger panels, contrary to the early-stage expectation that a size increase beyond 20 inches would be difficult. Major manufacturers have heretofore concentrated their efforts on the manufacture of small panels of 20 inches and smaller. Responsive to such a trend in recent years, however, they are now actively introducing latest technologies to expand their product range to larger sizes of 20 inches and greater.

As mentioned above, there is a trend toward larger glass panels for use in combination with various optical films upon manufacture of liquid crystal display panels. If a defective product occurs at the time of initial bonding of an optical film to a liquid crystal cell, the optical film may be removed from the liquid crystal cell, and then, the liquid crystal cell may be washed to permit its reuse. If a conventional pressure-sensitive adhesive having high adhesiveness is used, this high adhesiveness makes it difficult to remove the optical film upon its separation due to the high adhesiveness force and moreover, is accompanied by a high potential risk of breaking the costly liquid cell. As a consequence, the use of such a conventional pressure-sensitive adhesive leads to a significant increase in manufacturing cost.

Keeping in step with the move toward larger LCDs, attempts have, therefore, been continued to develop high-function pressure-sensitive adhesives capable of satisfying various adhesion properties such as adhesiveness and rework capability. For example, Japanese Patent No. 3022993 proposes an epoxysilane-containing, acrylic pressure-sensitive adhesive composition for the purpose of providing a polarizer excellent in durability under an environment of high temperature and high humidity.

Further, JP-A 8-104855 proposes a pressure-sensitive adhesive composition containing an acrylic polymer and a compound which has a β-ketoester group and a hydrolyzable silyl group, not only to permit bonding a polarizer on the surface of a substrate with good adhesive force but also to permit removing the polarizer from the surface of the substrate as needed without giving damage to the substrate or allowing the adhesive to remain.

It is described that owing to the inclusion of such a silane compound, the substrate and the polarizer can retain adequate adhesive force of such a level as required in an actual use environment, the adhesive force does not become excessive by heating or the like, and the polarizer can be readily removed without giving damage to the liquid crystal device.

As performance required for a pressure-sensitive adhesive to support the move toward larger LCDs, it is necessary not only to produce low initial adhesive force upon bonding to glass and to assure excellent rework capability but also to develop high adhesive force under high temperature and high humidity. Otherwise, there is a potential problem that bubbling, separation and/or the like may take place to lower the durability.

JP-A 8-199144 proposes a technology that incorporates a curing agent in an acrylic resin which is obtainable by polymerizing an acrylic monomer in the presence of a silane compound to provide a pressure-sensitive adhesive composition that does not undergo much variations with time in cohesive force and adhesive force even under high temperature and high humidity and is also excellent in adhesive force for curved surfaces.

It is described that owing to the incorporation of the silane compound, the substrate and the polarizer can retain adequate adhesive force of such a level as required in an actual use environment, the adhesive force does not become excessive by heating or the like, and the polarizer can be readily removed without giving damage to the liquid crystal device.

However, a pressure-sensitive adhesive composition is considered to be preferred when it is high in adhesive force, free from bubbling or separation and excellent in durability rather than when it does not undergo much variations with time in cohesive force and adhesive force even under high temperature and high humidity. In other words, it is considered necessary to show adequate initial adhesive force of such a level as permitting removal of a polarizer in an initial stage after its bonding to glass but, as time goes on, to be enhanced in adhesive force and to retain stabilized adhesive force because it becomes no longer necessary to remove the polarizer.

As a pressure-sensitive adhesive low in initial adhesive force and excellent in rework capability, and after bonding, enhanced in adhesive force under high temperature and high humidity and excellent in durability over long term, JP-T 2008-506028 proposes an acrylic self-sensitive adhesive composition containing a silane coupling agent having a urethane functional group and a pyridine functional group.

However, the silane coupling agent is obtained by reacting an isocyanatosilane and 2-pyridinol in the presence of a catalyst, and a hydroxyl group of 2-pyridinol non-selectively reacts to both the isocyanato group and hydrolyzable silyl group of the silane. Accordingly, the silane coupling agent does not have such a single structure as the disclosed silane, and is insufficient in the improvements of various self-adhesion properties.

Under the foregoing circumstances, it has been desired to develop a pressure-sensitive adhesive which has rework capability in an initial stage and retains high adhesiveness force under high temperature and high humidity.

CITATION LIST

Patent Document 1: Japanese Patent No. 3022993
Patent Document 2: JP-A 8-104855
Patent Document 3: JP-A 8-199144
Patent Document 4: JP-T 2008-506028

SUMMARY OF THE INVENTION

It is therefore an object of the present invention to provide an organosilicon compound capable of affording a pressure-sensitive adhesive composition which can form a pressure-sensitive adhesive layer having low initial adhesiveness force and excellent rework capability upon bonding an optical film or the like on an adherend such as glass and exhibiting increased adhesive force with the adherend and excellent long-term durability under conditions of high temperature or high temperature and high humidity after the bonding; and a production process of the organosilicon compound. Another object of the present invention is to provide a pressure-sensitive adhesive composition with such an organosilicon compound incorporated therein, a self-adhesive polarizer having a pressure-sensitive adhesive layer formed from the pressure-sensitive adhesive composition and a liquid crystal display having the self-adhesive polarizer.

To achieve the above-described objects, the present inventor has enthusiastically conducted investigations. As a result, it has been found that a pressure-sensitive adhesive composition which satisfies both rework capability in an initial stage and high adhesiveness force under high temperature or high temperature and high humidity can be obtained by incorporating in an adhesive composition a silane coupling agent having two or more functional groups equipped with coordination property with active hydrogen atoms in hydroxyl groups or the like and represented by one of the following formulas (1) to (3), leading to the completion of the present invention.

The present invention, therefore, provides the following organosilicon compounds, production processes thereof, pressure-sensitive adhesive composition, self-adhesive polarizer, and liquid crystal display.

[1] An organosilicon compound represented by the following formula (1):

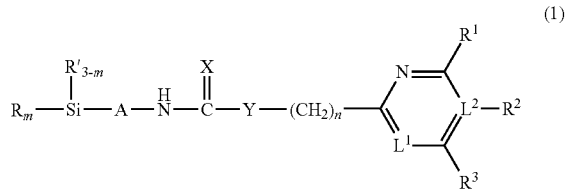

wherein R is a hydrolyzable group, R' is an alkyl group having 1 to 4 carbon atoms, A is a linear or branched alkylene group having 1 to 6 carbon atoms, X is an oxygen atom or sulfur atom, Y is —NH— or a sulfur atom, $L^1$ and $L^2$ are each independently a carbon atom or nitrogen atom, $R^1$ to $R^3$ are each independently a hydrogen atom, an alkyl, alkoxy or fluoroalkyl group having 1 to 6 carbon atoms, or an amino group, $R^1$ and $R^2$ or $R^2$ and $R^3$ may bond together to form a ring skeleton with the carbon atoms to which they are bonded and $L^2$, m is an integer of 1 to 3, and n is an integer of 0 to 3.

[2] An organosilicon compound represented by the following formula (2):

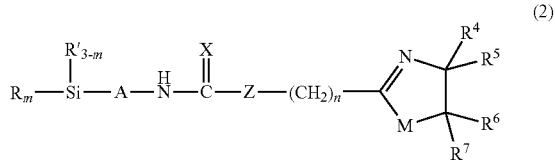

wherein R is a hydrolyzable group, R' is an alkyl group having 1 to 4 carbon atoms, A is a linear or branched alkylene group having 1 to 6 carbon atoms, X is an oxygen atom or sulfur atom, Z is —NH—, an oxygen atom or a sulfur atom, M is —NH—, an oxygen atom or a sulfur atom, $R^4$ to $R^7$ are each independently a hydrogen atom, an alkyl, alkoxy or fluoroalkyl group having 1 to 6 carbon atoms, or an amino group, $R^5$ and $R^6$ may directly bond together to form a double bond between the carbon atoms to which they are bonded, $R^4$ and $R^7$ may bond together to form an aliphatic or aromatic ring skeleton together with the carbon atoms to which they are bonded, m is an integer of 1 to 3, and n is an integer of 0 to 3.

[3] An organosilicon compound represented by the following formula (3):

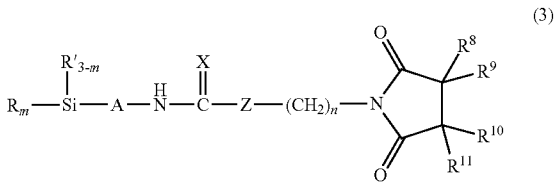

wherein R is a hydrolyzable group, R' is an alkyl group having 1 to 4 carbon atoms, A is a linear or branched alkylene group having 1 to 6 carbon atoms, X is an oxygen atom or sulfur atom, Z is —NH—, an oxygen atom or a sulfur atom, $R^8$ to $R^{11}$ are each independently a hydrogen atom, an alkyl, alkoxy or fluoroalkyl group having 1 to 6 carbon atoms, or an amino group, $R^9$ and $R^{10}$ may directly bond together to form a double bond between the carbon atoms to which they are bonded, $R^8$ and $R^{11}$ may bond together to form an aliphatic or aromatic ring skeleton together with the carbon atoms to which they are bonded, m is an integer of 1 to 3, and n is an integer of 0 to 3.

[4] A process for producing the organosilicon compound as described above [1], which includes reacting an iso(thio) cyanatosilane, which is represented by the following formula (4):

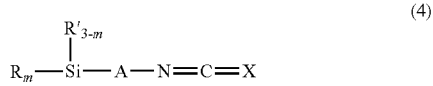

(4)

wherein R is a hydrolyzable group, R' is an alkyl group having 1 to 4 carbon atoms, A is a linear or branched alkylene group having 1 to 6 carbon atoms, X is an oxygen atom or sulfur atom, and m is an integer of 1 to 3, with a heterocyclic compound represented by the following formula (5):

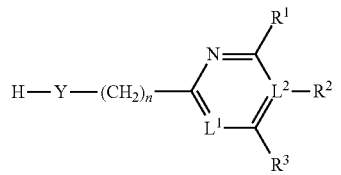

(5)

wherein Y is —NH— or a sulfur atom, $L^1$ and $L^2$ are each independently a carbon atom or nitrogen atom, $R^1$ to $R^3$ are each independently a hydrogen atom, an alkyl, alkoxy or fluoroalkyl group having 1 to 6 carbon atoms, or an amino group, $R^1$ and $R^2$ or $R^2$ and $R^3$ may bond together to form a ring skeleton with the carbon atoms to which they are bonded and $L^2$, and n is an integer of 0 to 3.

[5] A process for producing the organosilicon compound as described above [2], which includes reacting an iso(thio) cyanatosilane, which is represented by the following formula (4):

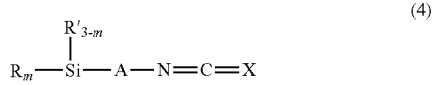

(4)

wherein R is a hydrolyzable group, R' is an alkyl group having 1 to 4 carbon atoms, A is a linear or branched alkylene group having 1 to 6 carbon atoms, X is an oxygen atom or sulfur atom, and m is an integer of 1 to 3, with a heterocyclic compound represented by the following formula (6):

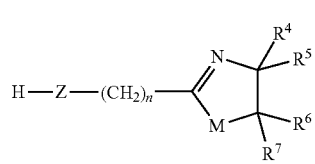

(6)

wherein Z is —NH—, an oxygen atom or a sulfur atom, M is —NH—, an oxygen atom or a sulfur atom, $R^4$ to $R^7$ are each independently a hydrogen atom, an alkyl, alkoxy or fluoroalkyl group having 1 to 6 carbon atoms, or an amino group, $R^5$ and $R^6$ may directly bond together to form a double bond between the carbon atoms to which they are bonded, $R^4$ and $R^7$ may bond together to form an aliphatic or aromatic ring skeleton together with the carbon atoms to which they are bonded, and n is an integer of 0 to 3.

[6] A process for producing the organosilicon compound as described above [3], which includes reacting an iso(thio) cyanatosilane represented by the following formula (4):

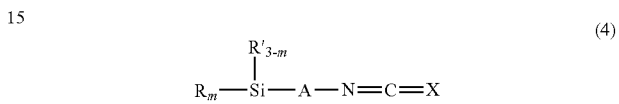

(4)

wherein R is a hydrolyzable group, R' is an alkyl group having 1 to 4 carbon atoms, A is a linear or branched alkylene group having 1 to 6 carbon atoms, X is an oxygen atom or sulfur atom, and m is an integer of 1 to 3, with a heterocyclic compound represented by the following formula (7):

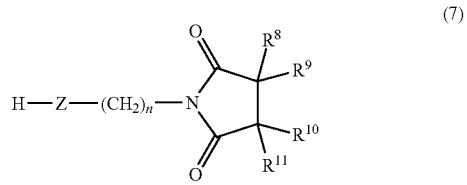

(7)

wherein Z is —NH—, an oxygen atom or a sulfur atom, $R^8$ to $R^{11}$ are each independently a hydrogen atom, an alkyl, alkoxy or fluoroalkyl group having 1 to 6 carbon atoms, or an amino group, $R^9$ and $R^{10}$ may directly bond together to form a double bond between the carbon atoms to which they are bonded, $R^8$ and $R^{11}$ may directly bond together to form an aliphatic or aromatic ring skeleton together with the carbon atoms to which they are bonded, and n is an integer of 0 to 3.

[7] A pressure-sensitive adhesive composition including the organosilicon compound as described any one of above [1] to [3].

[8] The pressure-sensitive adhesive composition as described above [7], including:

(A) 100 parts by weight of a (meth)acrylic copolymer obtainable by copolymerizing (a) 90 to 99.9 parts by weight of a (meth)acrylate ester monomer having an alkyl group having 1 to 12 carbon atoms and (b) 0.1 to 10 parts by weight of at least one of a vinyl monomer and (meth)acrylic monomer each of which contains a crosslinkable functional group, (B) 0.01 to 10 parts by weight of a polyfunctional crosslinking agent, and (C) 0.01 to 9 parts by weight of organosilicon compounds as described any one of above [1] to [3].

[9] The pressure-sensitive adhesive composition as described above [8], wherein at least one of the vinyl monomer and (meth)acrylic monomer (b) is selected from a group consisting of 2-hydroxyethyl(meth)acrylate, 3-hydroxypropyl(meth)acrylate, 4-hydroxybutyl(meth)acrylate, diethylene glycol mono(meth)acrylate, dipropylene glycol mono (meth)acrylate, (meth)acryloxypropyltrimethoxysilane, (meth)acryloxypropyltriethoxysilane, (meth)acryloxypropylmethyldimethoxysilane, (meth)acryloxypropylmethyldiethoxysilane, (meth)acryloxymethyltrimethoxysilane, (meth)acryloxymethyltriethoxysilane, (meth)acryloxymethylmethyldimethoxysilane, (meth)acryloxymethylmethyldiethoxysilane, (meth)acrylic acid, (meth)acrylic acid dimmer, itaconic acid, maleic acid, and maleic acid anhydride.

[10] The pressure-sensitive adhesive composition as described above [8] or [9], wherein the polyfunctional crosslinking agent (B) is at least one crosslinking agent selected from a group consisting of isocyanate compounds, epoxy compounds, aziridine compounds and metal chelate compounds.

[11] The pressure-sensitive adhesive composition as described above [7], which is cured into a product having a crosslink density of 5 to 95 wt %.

[12] A self-adhesive polarizer including a polarizing film and a pressure-sensitive adhesive layer formed from the pressure-sensitive adhesive composition as described above [7] and applied on at least one of opposite sides of the polarizing film.

[13] The self-adhesive polarizer as described above [12], further including at least one layer selected from a group consisting of a protective layer, a reflective layer, a retardation plate, an optical view-angle compensation film, and a luminance enhancement film.

[14] A liquid crystal display including a liquid crystal cell composed of a pair of glass substrates and a liquid crystal sealed between the glass substrates and the self-adhesive polarizer as described above [12] or [13] bonded on at least one of opposite sides of the liquid crystal cell.

ADVANTAGEOUS EFFECT OF THE INVENTION

Each organosilicon compound (silane coupling agent) according to the present invention has organic functional groups excellent in coordination property with active protons like hydrogen atoms in hydroxyl groups. A self-sensitive adhesive composition with the organosilicon compound incorporated therein is excellent in rework capability in an initial stage because hydrogen bonds are formed between active protons in chains on the side of a base polymer and the functional groups in the silane coupling agent. Moreover, the adhesive force increases with time under high temperature or high temperature and high humidity so that the self-sensitive adhesive composition is excellent in long-term durability.

DETAILED DESCRIPTION OF THE PREFERRED EMBODIMENTS

Figure 1:
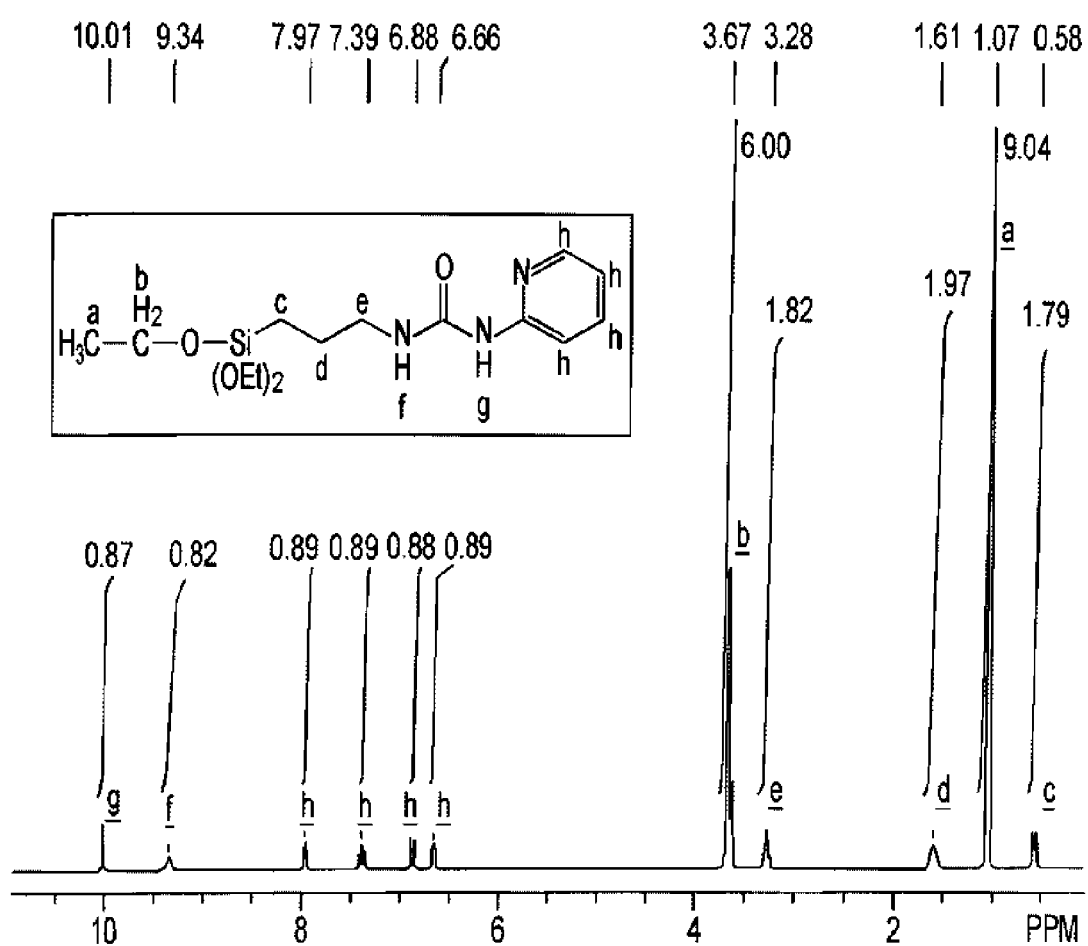
FIG. 1 is a diagram showing a $^1$H-NMR spectrum of the reaction product of Synthesis Example 1.

A description will hereinafter be made specifically about the present invention. It is to be noted that the term "silane coupling agent" as used herein is embraced in the term "organosilicon compound."

Organosilicon Compounds (Silane Coupling Agents)

As a characteristic feature of each organosilicon compound (silane coupling agent) according to the present invention, it is possible to mention that it has all of the following structures (i) to (iii):
(i) a heterocycle having at least one atom selected from nitrogen atoms, oxygen atoms and sulfur atoms;
(ii) a divalent organic group containing at least one bond selected from (thio)urethane bond, (thio)urea bond, (thio)amide bond, (thio)ester bond, amino bond, (thio)ether bond and sulfide bond; and
(iii) a hydrolyzable silyl group.

The heterocycle of the structure (i), which has at least one of nitrogen atoms, oxygen atoms and sulfur atoms, can be an aliphatic ring or aromatic ring. Its specific structures include, but are not limited to, structures such as those to be described below.

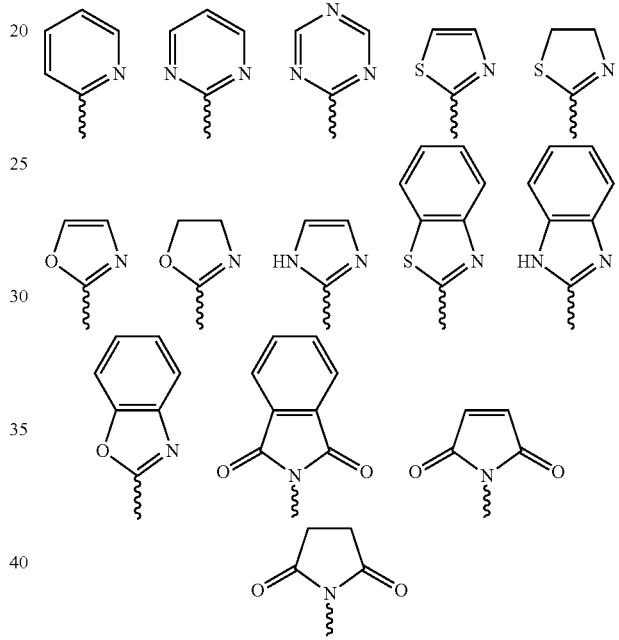

wherein wavy lines indicate bonds.

In the present invention, no particular limitation is imposed on the hydrolyzable silyl group of the structure (iii) insofar as it is a silyl group having at least one of a monovalent hydrolyzable atom bonded directly to a silicon atom (an atom capable of forming a silanol group through a reaction with water) and a monovalent hydrolyzable group bonded directly to a silicon atom (a group capable of forming a silanol group through a reaction with water). Such a hydrolyzable silyl group undergoes hydrolysis to form a silanol group, and this silanol group undergoes dehydration condensation with an inorganic material to form a chemical bond of the formula: Si—O—M (M: inorganic material). Each organosilicon compound according to the present invention contains only one of such a hydrolyzable silyl group, and may contain two or more of such hydrolyzable silyl groups. When two or more hydrolyzable silyl groups exist, they may be the same or different.

Examples of the hydrolyzable silyl group of the structure (iii) include chlorosilyl, bromosilyl, methoxysilyl, ethoxysilyl, propoxysilyl, butoxysilyl, and the like.

Preferred silane coupling agents according to the present invention include those represented by the following formulas (1) to (3):

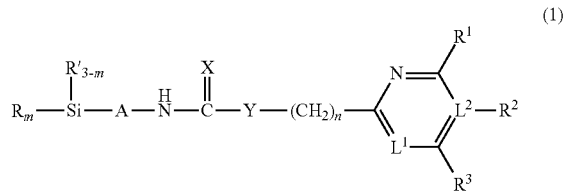

(1)

wherein R is a hydrolyzable group, R' is an alkyl group having 1 to 4 carbon atoms, A is a linear or branched alkylene group having 1 to 6 carbon atoms, X is an oxygen atom or sulfur atom, Y is —NH— or a sulfur atom, $L^1$ and $L^2$ are each independently a carbon atom or nitrogen atom, $R^1$ to $R^3$ are each independently a hydrogen atom, an alkyl, alkoxy or fluoroalkyl group having 1 to 6 carbon atoms, or an amino group, $R^1$ and $R^2$ or $R^2$ and $R^3$ may bond together to form a ring skeleton with the carbon atoms to which they are bonded and $L^2$, m is an integer of 1 to 3, and n is an integer of 0 to 3;

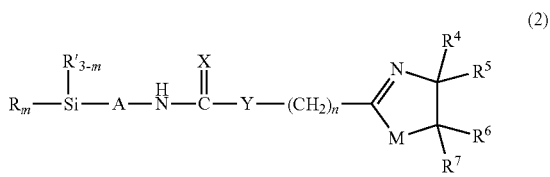

(2)

wherein R, R', A, X, m and n are as defined above, Z is —NH—, an oxygen atom or a sulfur atom, M is —NH—, an oxygen atom or a sulfur atom, $R^4$ to $R^7$ are each independently a hydrogen atom, an alkyl, alkoxy or fluoroalkyl group having 1 to 6 carbon atoms, or an amino group, $R^5$ and $R^6$ may directly bond together to form a double bond between the carbon atoms to which they are bonded, and $R^4$ and $R^7$ may bond together to form an aliphatic or aromatic ring skeleton together with the carbon atoms to which they are bonded; and

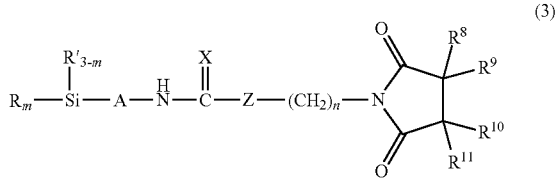

(3)

wherein R, R', A, X, Z, m and n are as defined above, $R^8$ to $R^{11}$ are each independently a hydrogen atom, an alkyl, alkoxy or fluoroalkyl group having 1 to 6 carbon atoms, or an amino group, $R^9$ and $R^{10}$ may directly bond together to form a double bond between the carbon atoms to which they are bonded, and $R^8$ and $R^{11}$ may directly bond together to form an aliphatic or aromatic ring skeleton together with the carbon atoms to which they are bonded.

In the above-described formulas, R can be a halogen atom such as chlorine or bromine, or an alkoxy group such as methoxy, ethoxy, propoxy or butoxy; and R' can be an alkyl group such as methyl, ethyl or propyl. A can be, but is not limited to, a linear alkylene group such as methylene, ethylene or propylene, or a branched alkylene group such as methallyl, isopropylene or isobutylene. Further, $R^1$ to $R^3$ can each be a hydrogen atom, an alkyl group such as methyl, ethyl or propyl, a fluoroalkyl group formed by substituting some or all of the hydrogen atoms of such a group with a like number of fluorine atoms, an alkoxy group such as methoxy, ethoxy or propoxy, or an amino group; or $R^1$ and $R^2$ or $R^2$ and $R^3$ may bond together with the carbon atoms to which they are bonded to form a ring such as cyclopentyl or cyclohexyl. $R^4$ to $R^7$ can each be a hydrogen atom, an alkyl group such as methyl, ethyl or propyl, a fluoroalkyl group formed by substituting some or all of the hydrogen atoms of such a group with a like number of fluorine atoms, an alkoxy group such as methoxy, ethoxy or propoxy, or an amino group; or $R^5$ and $R^6$ may directly bond together to form a double bond between the carbon atoms to which they are bonded, and/or $R^4$ and $R^7$ may bond together to form an aliphatic or aromatic ring skeleton together with the carbon atoms to which they are bonded. $R^8$ to $R^{11}$ can each be a hydrogen atom, an alkyl group such as methyl, ethyl or propyl, a fluoroalkyl group formed by substituting some or all of the hydrogen atoms of such a group with a like number of fluorine atoms, an alkoxy group such as methoxy, ethoxy or propoxy, or an amino group; or $R^9$ and $R^{10}$ may directly bond together to form a double bond between the carbon atoms to which they are bonded, and/or $R^8$ and $R^{11}$ may bond together to form an aliphatic or aromatic ring skeleton such as cyclopentyl or cyclohexyl together with the carbon atoms to which they are bonded.

Specific examples of the silane coupling agents having coordinate function groups according to the present invention are represented by the following structural formulas (8) to (15), in which Et represents an ethyl group.

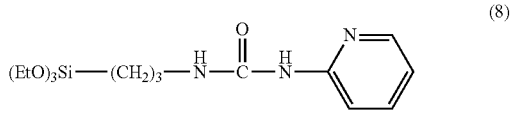

(8)

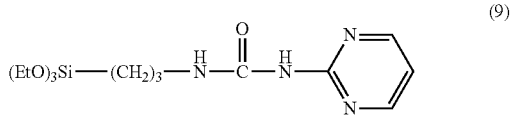

(9)

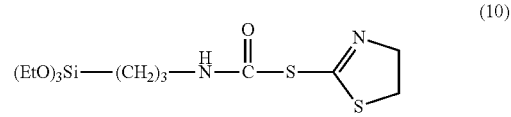

(10)

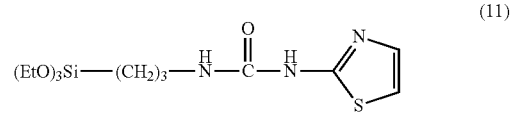

(11)

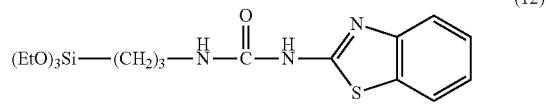

(12)

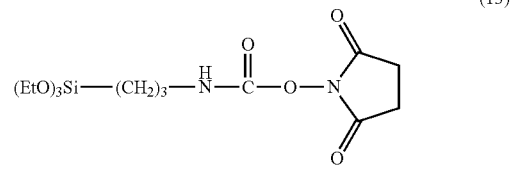

(13)

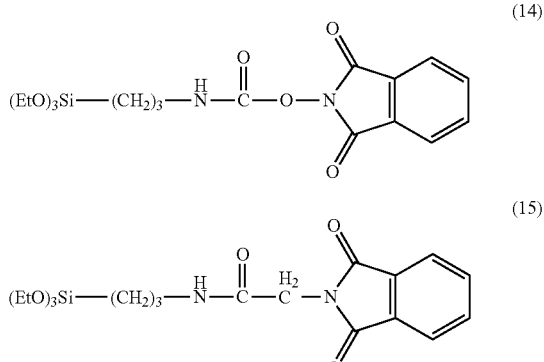

The above-described silane coupling agents can each form, with an active proton such as the hydrogen atom in a hydroxyl group, a stable coordinate bond such as that represented by the following formula (A):

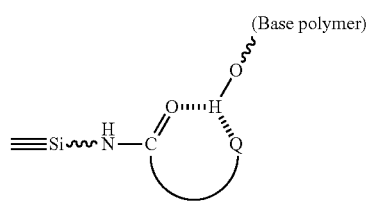

wherein Q represents a nitrogen atom, sulfur atom, or oxygen atom.

The silane coupling agents according to the present invention can each be obtained by reacting an iso(thio)cyanatosilane coupling agent, which is represented by the following formula (4):

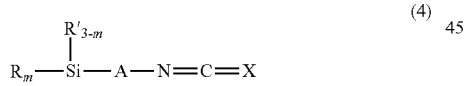

wherein R is a hydrolyzable group, R' is an alkyl group having 1 to 4 carbon atoms, A is a linear or branched alkylene group having 1 to 6 carbon atoms, X is an oxygen atom or sulfur atom, and m is an integer of 1 to 3, with one of amine compound, mercapto compound and alcohol having heterocyclic structures and represented by the below-described formulas (5) to (7).

The iso(thio)cyanatosilane can be commercially available. Specific examples include, but are not limited to, isocyanatomethyltrimethoxysilane, isocyanatomethyltriethoxysilane, isocyanatoethyltrimethoxysilane, isocyanatoethyltriethoxysilane, isocyanatopropyltrimethoxysilane, isocyanatopropyltriethoxysilane, isothiocyanatopropyltriethoxysilane, and the like.

The amine compound, mercapto compound and alcohol having the heterocyclic structures can be compounds represented by the below-described formulas (5) to (7).

wherein Y is —NH— or a sulfur atom, $L^1$ and $L^2$ are each independently a carbon atom or nitrogen atom, $R^1$ to $R^3$ are each independently a hydrogen atom, an alkyl, alkoxy or fluoroalkyl group having 1 to 6 carbon atoms, or an amino group, $R^1$ and $R^2$ or $R^2$ and $R^3$ may bond together to form a ring skeleton with the carbon atoms to which they are bonded and $L^2$, and n is an integer of 0 to 3;

wherein Z is —NH—, an oxygen atom or a sulfur atom, M is —NH—, an oxygen atom or a sulfur atom, $R^4$ to $R^7$ are each independently a hydrogen atom, an alkyl, alkoxy or fluoroalkyl group having 1 to 6 carbon atoms, or an amino group, $R^5$ and $R^6$ may directly bond together to form a double bond between the carbon atoms to which they are bonded, $R^4$ and $R^7$ may bond together to form an aliphatic or aromatic ring skeleton together with the carbon atoms to which they are bonded, and n is an integer of 0 to 3; and wherein Z is —NH—, an oxygen atom or a sulfur atom, $R^8$ to $R^{11}$ are each independently a hydrogen atom, an alkyl, alkoxy or fluoroalkyl group having 1 to 6 carbon atoms, or an amino group, $R^9$ and $R^{10}$ may directly bond together to form a double bond between the carbon atoms to which they are bonded, $R^8$ and $R^{11}$ may bond together to form an aliphatic or aromatic ring skeleton together with the carbon atoms to which they are bonded, and n is an integer of 0 to 3.

In the above-described formulas, $R^1$ to $R^{11}$ can be similar to those described above. These compounds having the heterocyclic structures can be those available on the market. Specific examples include, but are not limited to, aminoimidazole, mercaptoimidazole, hydroxyimidazole, aminothiazole, mercaptothiazole, hydroxythiazole, aminothiazoline, mercaptothiazoline, hydroxythiazoline, aminopyridine, mercaptopyridine, hydroxypyridine, aminopyrimidine, mercaptopyrimidine, hydroxypyrimidine, aminotriazine, mercaptotriazine, hydroxytriazine, aminobenzothiazole, hydroxysuccinimide, hydroxyphthalimide, hydroxymethylphthalimide, and the like.

Upon producing each silane coupling agent according to the present invention, no particular limitation is imposed on the mixing ratio of the amine compound, mercapto compound or alcohol having the heterocyclic structure to the iso(thio)cyanatosilane. From the standpoints of reactivity and productivity, however, it is preferred to react the amine compound, mercapto compound or alcohol having the heterocyclic structure in a range of from 0.5 to 2 moles, especially from 0.8 to 1.2 moles per mole of the iso(thio)cyanatosilane. If the mixing amount of the compound having the heterocyclic structure is too little, the iso(thio)cyanatosilane may remain abundantly and may undergo polymerization to cause gelling. If too much, on the other hand, no effects are given to various properties of the resulting silane coupling agent, but demerits may arise such that the resulting silane coupling agent would be provided with lowered purity and moreover, its productivity would be reduced.

Upon producing each silane coupling agent according to the present invention, an organic solvent may be used as needed. Described specifically, no particular limitation is imposed on the organic solvent, insofar as it is reactive with neither the iso(thio)cyanato group and hydrolyzable silyl group in the reactant iso(thio)cyanatosilane coupling agent nor the amino group, mercapto or hydroxyl group in the reactant amine compound, mercapto compound or alcohol. More specific examples include, but are not limited to, aliphatic hydrocarbon solvents such as pentane, hexane and heptane; aromatic hydrocarbon solvents such as toluene and xylene; linear or cyclic ether solvents such as diethyl ether, cyclopentyl methyl ether, dioxane and tetrahydrofuran; ester solvents such as ethyl acetate and butyl acetate; amide solvents such as formamide, dimethylformamide, pyrrolidone and N-methylpyrrolidone; ketone solvents such as acetone, methyl ethyl ketone, methyl isobutyl ketone and cyclohexanone; and the like.

Upon producing each silane coupling agent according to the present invention, a reaction catalyst may be used as needed. In general, use of no catalyst in the reaction between an isocyanate compound and a mercapto compound or alcohol may lead to low reaction velocity and inferior productivity. The reaction catalyst can be commercially available. Specifically, organotin compounds are preferred, with octyltin compounds and organotin compounds having one or more substituent groups having at least 8 carbon atoms being more preferred in view of environmental load, although the reaction catalyst is not limited to those exemplified above.

No particular limitation is imposed on the amount of the catalyst to be used. From the standpoints of reactivity and productivity, however, it is preferred to use the catalyst in a range of from 0.00001 to 0.1 parts by weight, notably from 0.0001 to 0.01 parts by weight per 1 part by weight of the silane compound. The use of the catalyst in an amount in this range makes it easier to bring about sufficient reaction promoting effect commensurate with the amount of the catalyst.

No particular limitation is imposed on the reaction temperature insofar as the iso(thio)cyanato group and the amino group, mercapto or hydroxyl group can react with each other, although it may range preferably from 0 to 200° C., notably from 10 to 150° C. The reaction time may range preferably from 10 minutes to 10 hours, notably from 30 minutes to 6 hours. The atmosphere may preferably be the air atmosphere or an inert gas atmosphere such as nitrogen or argon.

As a result of the reaction between the iso(thio)cyanato group and the amino, mercapto or hydroxyl group, a (thio)urea bond or (thio)urethane bond having coordinate property is formed so that a silane coupling agent having coordinate functional groups is obtained.

Pressure-Sensitive Adhesive Composition

A description will next be made about the pressure-sensitive adhesive composition containing the above-described coordinate functional groups.

The pressure-sensitive adhesive composition according to the present invention may preferably include:
(A) 100 parts by weight of a (meth)acrylic copolymer obtainable by copolymerizing (a) 90 to 99.9 parts by weight of a (meth)acrylate ester monomer with an alkyl group having 1 to 12 carbon atoms and (b) 0.1 to 10 parts by weight of at least one of a vinyl monomer and (meth)acrylic monomer each of which contains a crosslinkable functional group,
(B) 0.01 to 10 parts by weight of a polyfunctional crosslinking agent, and
(C) 0.01 to 9 parts by weight of an organosilicon compound represented by any one of the formulas (1) to (3).

The (meth)acrylate ester monomer with an alkyl group having 1 to 12 carbon atoms (a) for use in the composition according to the present invention may be contained desirably in an amount of 90 to 99.9 parts by weight, notably in an amount of 91 to 99 parts by weight in 100 parts by weight of the monomers to be copolymerized. Its content lower than 90 parts by weight may lead to a reduction in initial adhesive force, while its content higher than 99.9 parts by weight may cause a problem in durability due to reduced cohesive force.

As the (meth)acrylate ester monomer with an alkyl group having 1 to 12 carbon atoms as component (a), it is possible to use a (meth)acrylate with an alkyl group having 1 to 12 carbon atoms other than the (meth)acrylic monomer containing a crosslinkable functional group as component (b), with the use of a (meth)acrylate with an alkyl group having 2 to 8 carbon atoms being more preferred. Namely, the alkyl(meth)acrylate provides the resulting pressure-sensitive adhesive with reduced cohesive force if its alkyl group is in the form of a long chain. To retain cohesive force under high temperatures, the carbon number of the alkyl group may be preferably in the range of from 1 to 12, more preferably in the range of from 2 to 8.

Specific examples of the (meth)acrylate ester monomer include butyl(meth)acrylate, 2-ethylhexyl(meth)acrylate, ethyl(meth)acrylate, methyl(meth)acrylate, n-propyl(meth)acrylate, isopropyl(meth)acrylate, t-butyl(meth)acrylate, pentyl(meth)acrylate, n-octyl(meth)acrylate, isooctyl(meth)acrylate, isononyl(meth)acrylate, and the like. These (meth)acrylate ester monomers can be used either alone or in combination of two or more.

The at least one of the vinyl monomer and (meth)acrylic monomer each of which contains the crosslinkable functional group as component (b) reacts with the crosslinking agent to impart cohesive force and adhesive force by chemical bonds such that no failure takes place in the cohesive force of the resulting pressure-sensitive adhesive under conditions of high temperature or high temperature and high humidity. As the mixing amount of the monomer as component (b), it may be used preferably in an amount of 0.1 to 10 parts by weight, notably 1 to 9 parts weight in 100 parts by weight of the monomers to be copolymerized. A mixing amount smaller than 0.1 parts by weight may induce a cohesion failure under high temperature and high humidity, while a mixing amount greater than 10 parts by weight may become a cause of a substantial decrease in compatibility and a surface migration so that flowability may decrease and cohesive force may increase, resulting in lowered stress relieving capacity.

Examples of the vinyl monomer and (meth)acrylic monomer each of which contains the crosslinkable functional group as component (b) include, but are not limited to, monomers containing one or more hydroxyl groups such as 2-hydroxyethyl(meth)acrylate, 3-hydroxypropyl(meth)acrylate, 4-hydroxybutyl(meth)acrylate, diethylene glycol mono(meth)acrylate and dipropylene glycol mono(meth)acrylate; monomers containing one or more carboxyl groups such as (meth)acrylic acid, (meth)acrylic acid dimer, itaconic acid, maleic acid and maleic acid anhydride; monomers containing a hydrolyzable silyl groups such as (meth)acryloxypropyltrimethoxysilane, (meth)acryloxypropyltriethoxysilane, (meth)acryloxypropylmethyldimethoxysilane, (meth)acryloxypropylmethyldiethoxysilane, (meth)acryloxymethyltrimethoxysilane, (meth)acryloxymethyltriethoxysilane, (meth)acryloxymethylmethyldimethoxysilane and (meth)acryloxymethylmethyldiethoxysilane; and the like. These monomers can be used either alone or in combination of two or more.

It is to be noted that in the present invention, copolymerizable monomers other than the above-described monomers can be additionally used upon production of the acrylic copolymer to adjust the glass transition point of the pressure-sensitive adhesive composition and also to impart other functionality. Described specifically, a copolymerizable monomer such as acrylonitrile, styrene, glycidyl(meth)acrylate or vinyl acetate can be used. The mixing amount of such a copolymerizable monomer may be preferably from 0.1 to 9.9 parts by weight, more preferably from 0.5 to 8 parts by weight in 100 parts by weight of the monomers to be copolymerized.

As viscoelastic properties of a pressure-sensitive adhesive composition are determined primarily by the molecular weight and molecular weight distribution of the polymer chain and the existing amount of the molecular structures, especially by the molecular weight. The molecular weight (weight average molecular weight: Mw) of the (meth)acrylic copolymer for use in the present invention may be preferably from 800,000 to 2,000,000, more preferably from 900,000 to 1,900,000. It is to be noted that each weight average molecular weight is a value as determined by gel permeation chromatography (GPC) using a polystyrene standard. An excessively low molecular weight may fail to obtain desired viscoelastic properties, while an unduly high molecular weight may provide the resultant polymer with very high viscosity to make its handling difficult so that the productivity may be lowered.

The copolymer can be produced through a conventional radical polymerization step. No particular limitation is imposed on the polymerization process of the copolymer in the present invention, and the copolymer can be produced by a general process such as solution polymerization, photopolymerization, bulk polymerization, suspension polymerization or emulsion polymerization. Of these, solution polymerization is preferred from the viewpoint of productivity. In solution polymerization, the polymerization temperature may preferably be from 50 to 140° C. and the reaction time may preferably be from 1 to 24 hours. It is preferred to add an initiator after the monomers have been formed into a uniform mixture.

In the pressure-sensitive adhesive composition according to the present invention, the polyfunctional crosslinking agent as component (B) plays a role to provide the resulting pressure-sensitive adhesive with enhanced cohesive force through its reaction with carboxyl groups and/or hydroxyl groups. The content of the crosslinking agent may be preferably from 0.01 to 10 parts by weight, more preferably from 0.05 to 5 parts by weight per 100 parts by weight of the copolymer as component (A). An unduly high content may result in severe cohesion so that the formation into a pressure-sensitive adhesive sheet or the like may be rendered difficult. An excessively low content, on the other hand, may fail to bring about the cohesive force enhancing effect as desired.

As the polyfunctional crosslinking agent, an isocyanate, epoxy, aziridine, metal chelate crosslinking agents can be used. Of these, an isocyanate crosslinking agent is easy to use. Specific examples of the isocyanate crosslinking agent include tolylene diisocyanate, xylene diisocyanate, diphenylmethane diisocyanate, hexamethylene diisocyanate, isoform diisocyanate, tetramethylxylene diisocyanate, naphthalene diisocyanate, and their reaction products with polyols such as trimethylolpropane.

Specific examples of the epoxy crosslinking agent include ethylene glycol diglycidyl ether, trimethylolpropane triglycidyl ether, N,N,N',N'-tetraglycidylethylenediamine, glycerin diglycidyl ether, glycerin triglycidyl ether, polyglycerin polyglycidyl ether, sorbitol polyglycidyl ethers, and the like.

Specific examples of the aziridine crosslinking agent include N,N'-toluene-2,4-bis(1-aziridinecarboxide), N,N'-diphenylmethane-4,4'-bis(1-aziridinecarboxide), triethylenemelamine, bisisoprotaloyl-1-(2-methylaziridine), tri-1-aziridinylphosphine oxide, and the like.

Examples of the metal chelate crosslinking agent include compounds that multivalent metals such as aluminum, iron, zinc, tin, titanium, antimony, magnesium and vanadium coordinate with acetyl acetone or ethyl acetoacetate, and the like.

As the organosilicon compound as component (C), it is preferred to use one of the above-described silane coupling agents having coordinate functional groups and represented by the formulas (1) to (3). By incorporating the silane coupling agent in the pressure-sensitive adhesive composition, the initial rework capability and the adhesive force under high temperature and high humidity are significantly improved. The specific structures of the silane coupling agents are as described above, and these silane coupling agents can be used either alone or in combination of two or more. Its mixing amount may be preferably from 0.01 to 9 parts by weight, more preferably from 0.1 to 5 parts by weight, particularly preferably from 0.1 to 3 parts by weight per 100 parts by weight of the (meth)acrylic copolymer (A). Its content lower than 0.01 parts by weight may not be able to fully bring about the advantageous effects available from the addition of the silane, while its content higher than 9 parts by weight involves a potential problem that due to its use in the excess amount, bubbles or separation may occur to result in reduced durability.

In the present invention, a tackiness-imparting resin can be added further to adjust the adhesion performance of the composition. Its content may be in a range of from 1 to 100 parts by weight, especially from 5 to 90 parts by weight per 100 parts by weight of the (meth)acrylic copolymer (A). A content lower than 1 parts by weight may not exhibit sufficient adjusting effect, while a content higher than 100 parts by weight involves a potential problem of providing the resulting adhesive with reduced common utility or cohesive property.

Usable examples of the tackiness-imparting resin include (hydrogenated) hydrocarbon resins, (hydrogenated) rosin resins, (hydrogenated) rosin ester resins, (hydrogenated) terpene resins, (hydrogenated) terpene phenol resins, polymerized rosin resins, polymerized rosin ester resins, and the like. They can be used either alone or in combination of two or more.

In addition to the above-described components, plasticizers, low-molecular-weight substances such as leveling agents, epoxy resins, curing agents and the like can be used as additional components in combination, and further, ultraviolet stabilizers, antioxidants, color removers, reinforcing agents, fillers, defoaming agent, surfactants and the like can be appropriately added and used depending on the application purpose.

No particular limitation is imposed on the production method of the pressure-sensitive adhesive composition according to the present invention, and the pressure-sensitive adhesive composition can be obtained by mixing (A) the (meth)acrylic copolymer, (B) the polyfunctional crosslinking agent and (C) the silane coupling agent in a usual manner. As mixing conditions, the mixing may be conducted preferably at 10 to 150° C. for 10 minutes to 10 hours. In this production, the silane coupling agent having the coordinate functional groups can be used by adding it in a mixing step after the polymerization of the (meth)acrylic copolymer. The silane coupling agent can exhibit the same effect even when it is added in the course of the production process of the (meth) acrylic copolymer. Further, uniform coating of the pressure-sensitive adhesive composition is feasible when no substantial crosslinking reactions of functional groups by the polyfunctional crosslinking agent take place in the mixing step conducted for the formation of a pressure-sensitive adhesive layer to be obtained by curing the pressure-sensitive adhesive composition. Through drying and aging steps after the coating, a crosslinked structure is formed so that a pressure-sensitive adhesive layer having elasticity and high cohesive force can be obtained.

The pressure-sensitive adhesive composition of this invention obtained as described above can form a pressure-sensitive adhesive layer when coated the composition on an adherend such as a glass plate, plastic film or paper sheet and cured at 25 to 150° C. and 20 to 90% RH for 5 minutes to 5 hours, especially at 40 to 80° C. and 25 to 60% RH for 10 minutes to 3 hours.

It is desired to use the pressure-sensitive adhesive composition of the invention after fully eliminating components which otherwise induce the formation of bubbles inside, such as volatile components and reaction residues. If the crosslink density and molecular weight are excessively low and the coefficient of elasticity of the pressure-sensitive adhesive layer is unduly low, small bubbles which exist between an adherend such as a glass plate and the pressure-sensitive adhesive layer become larger at a high-temperature to form scatterers inside the pressure-sensitive adhesive layer. If a pressure-sensitive adhesive layer having excessively high coefficient of elasticity is used over a long term, the pressure-sensitive adhesive layer (sheet) develops separation at end positions thereof due to excessive crosslinking reactions.

When an optimal physical balance is taken into consideration, the crosslink density of the pressure-sensitive adhesive layer may suitably be in a range of from 5 to 95 wt %, with a range of 7 to 93 wt % being particularly suited. The term "crosslink density" indicates a value that expresses portions where a crosslinked structure insoluble in a solvent is formed in terms of wt % by the commonly-known gel content measuring method for pressure-sensitive adhesives. If the crosslink density of a pressure-sensitive adhesive layer is lower than 5 wt %, the pressure-sensitive adhesive layer is provided with reduced cohesive force and therefore is accompanied by a potential problem in adhesion durability such as bubbling or separation. If higher than 95 wt %, on the other hand, the pressure-sensitive adhesive layer may not adhere firmly and may hence be reduced in durability.

Self-Adhesive Polarizer

A description will next be described about a self-adhesive polarizer including pressure-sensitive adhesive layer(s) obtained by coating and curing the pressure-sensitive adhesive composition on one or both of opposite sides of a polarizing film or the like.

The self-adhesive polarizer according to the present invention includes a polarizing film or polarizing device and pressure-sensitive adhesive layer(s) formed from the above-described pressure-sensitive adhesive composition and applied on one or both of opposite sides of the polarizing film or polarizing device. No particular limitation is imposed on the polarizing film or polarizing devices that constitutes the polarizer. Examples of the polarizing film include films obtained by incorporating a polarizing component such as iodine or a heterochromatic dye in films made of a polyvinyl alcohol resin and then stretching the films. No particular limitation is imposed on the thickness of these polarizing films, so that they can be formed with a usual thickness.

As the polyvinyl alcohol resin, polyvinyl alcohol, polyvinyl formal, polyvinyl acetal, a saponification production of an ethylene-vinyl acetate copolymer, or the like can be used.

As the polarizing film, it is also possible to use such a multilayer film that on opposite sides of a polarizing film, protective films, for example, cellulose films such as triacetyl cellulose films, polyester films such as polycarbonate films or polyethylene terephthalate films, polyethersulfone films, or polyolefin films such as polyethylene films, polypropylene films or ethylene-propylene copolymer films are laminated. No particular limitation is imposed on the thickness of these protective films, so that they can be formed with a usual thickness.

In the present invention, no particular limitation is imposed on the method for forming the pressure-sensitive adhesive layer on the polarizing film. It is possible to adopt, for example, such a method that includes coating the pressure-sensitive adhesive composition directly onto the surface of the polarizing film with a bar coater or the like and drying the thus-coated adhesive composition or such a method that includes once coating the pressure-sensitive adhesive composition onto a surface of a peelable base material and drying the thus-coated adhesive composition, transferring the pressure-sensitive adhesive layer, which has been formed on the surface of the peelable base material, onto the surface of the polarizing film, and then aging the thus-transferred adhesive layer. In this method, the drying may be conducted preferably at 25 to 150° C. and 20 to 90% RH for 5 minutes to 5 hours, and the aging may be conducted preferably at 25 to 150° C. and 20 to 90% RH for 5 minutes to 5 hours.

No particular limitation is imposed on the thickness of the pressure-sensitive adhesive layer. In general, however, the thickness may be preferably from 0.01 to 100 μm, more preferably from 0.1 to 50 μm. If the thickness of the pressure-sensitive adhesive layer is smaller than the above-described range, its effect as the pressure-sensitive adhesive layer may not be brought about fully. If the thickness of the pressure-sensitive adhesive layer is greater than the above-described range, on the other hand, the effect of the pressure-sensitive adhesive layer may reach saturation and may result in higher cost.

On the polarizing film with the pressure-sensitive adhesive layer applied thereon as described above (on the self-adhesive polarizer according to the present invention), it is possible to laminate one or more of layers providing additional functions such as a protective layer, a reflective layer, a retardation film, an optical view-angle compensation film, and a luminance enhancement film.

Liquid Crystal Display

The self-adhesive polarizer according to the present invention can be applied specifically to any one of usual liquid crystal displays, and no particular limitation is imposed on the kind of its liquid crystal panel. In particular, it is preferred to construct a liquid crystal display by including a liquid crystal panel with one or two self-adhesive polarizers of the present invention bonded on one or both of opposite sides of a liquid crystal cell composed of a pair of glass substrates and a liquid crystal sealed therebetween.

The self-adhesive composition according to the present invention can be used irrespective of applications, especially to industrial sheets such as, in addition to the above-described polarizing films, reflecting sheets, structural self-adhesive sheets, photographic self-adhesive sheets, lane-marking self-adhesive sheets, optical self-adhesive products, and electronic parts and components. It can also be used in application fields which are similar in action concept such as laminated products of multilayer structures, specifically general commercial self-adhesive sheet products, medical patches, heat activable products, and the like.

The pressure-sensitive adhesive composition according to the present invention is a (meth)acrylic pressure-sensitive adhesive containing a silane coupling agent having coordinate functional groups. As its initial adhesive force is low upon boding to glass or the like, rework capability is excellent. After moisture/heat exposure subsequent to the bonding, sufficiently high adhesive force is developed to provide excellent long-term durability.

EXAMPLES

The present invention will hereinafter be described more specifically based on Synthesis Examples, Examples and Comparative Examples, although the present invention shall not be limited to these Examples. It is to be noted that in the following examples, viscosities, specific gravities and refractive indexes are values measured as 25° C. Further, "NMR," "IR" and "GPC" are abbreviations of nuclear magnetic resonance spectroscopy, infrared spectroscopy and gel permeation chromatography, respectively. Viscosities are based on measurements at 25° C. by a capillary kinematic viscometer.

Synthesis Example 1

Figure 2:
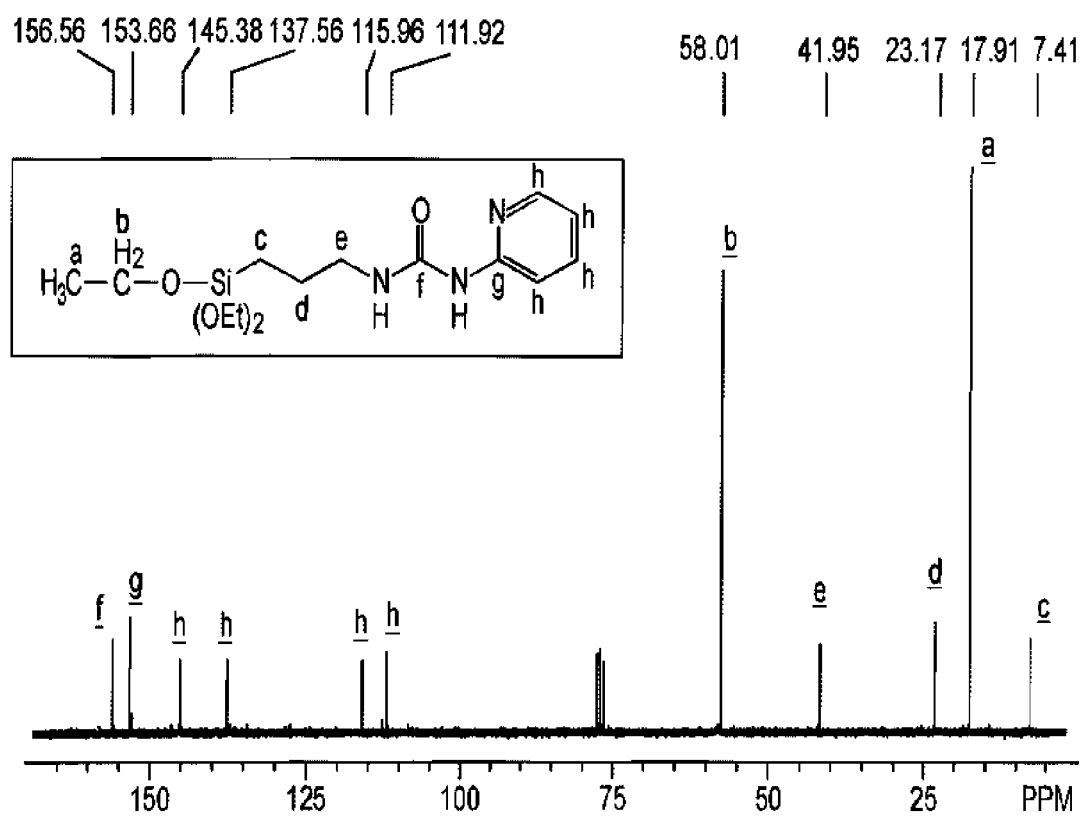
FIG. 2 is a diagram showing a $^{13}$C-NMR spectrum of the reaction product of Synthesis Example 1.
Figure 3:
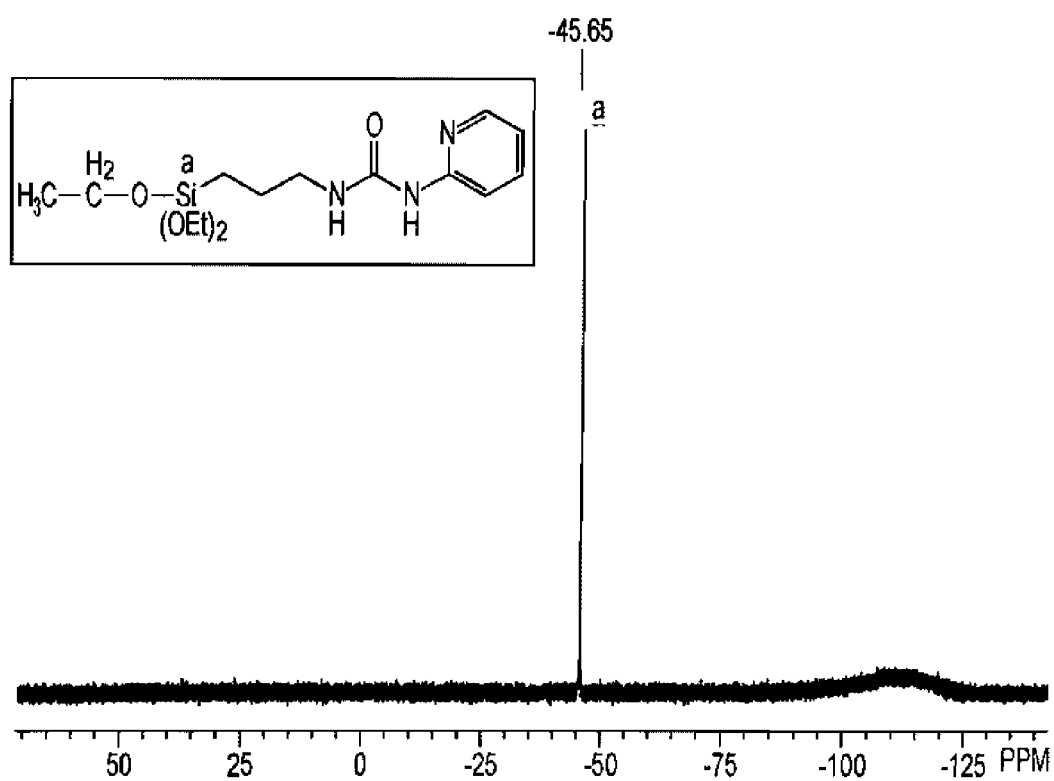
FIG. 3 is a diagram showing a $^{29}$Si-NMR spectrum of the reaction product of Synthesis Example 1.
Figure 4:
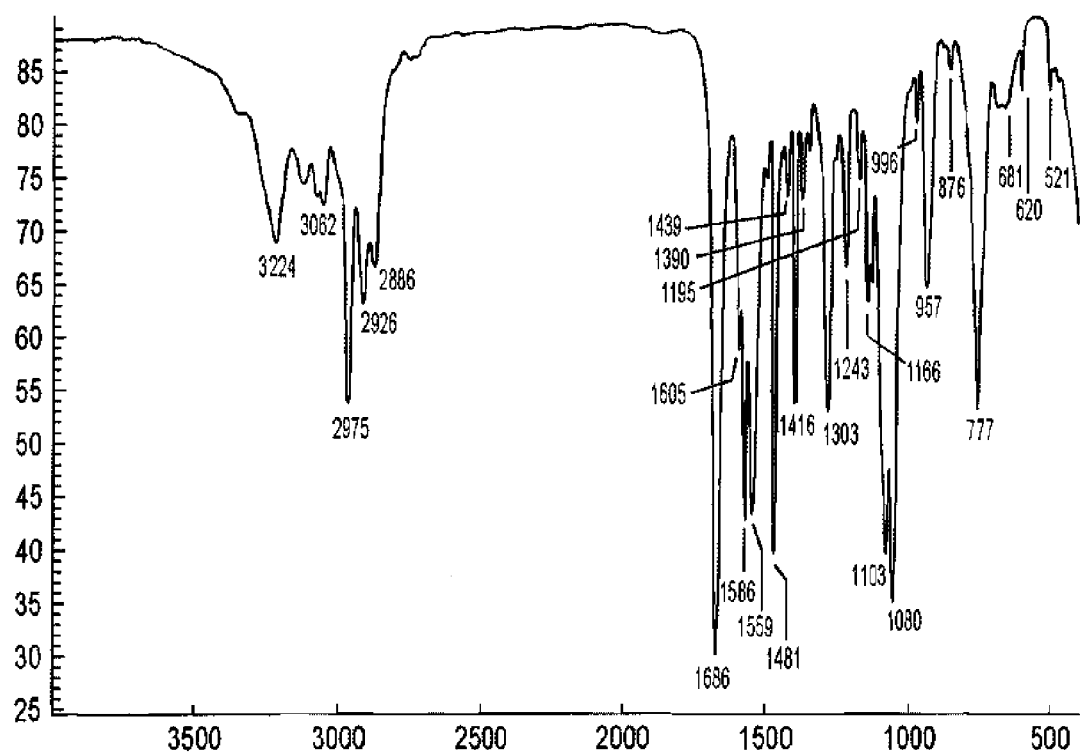
FIG. 4 is a diagram showing an IR spectrum of the reaction product of Synthesis Example 1.
Figure 5:
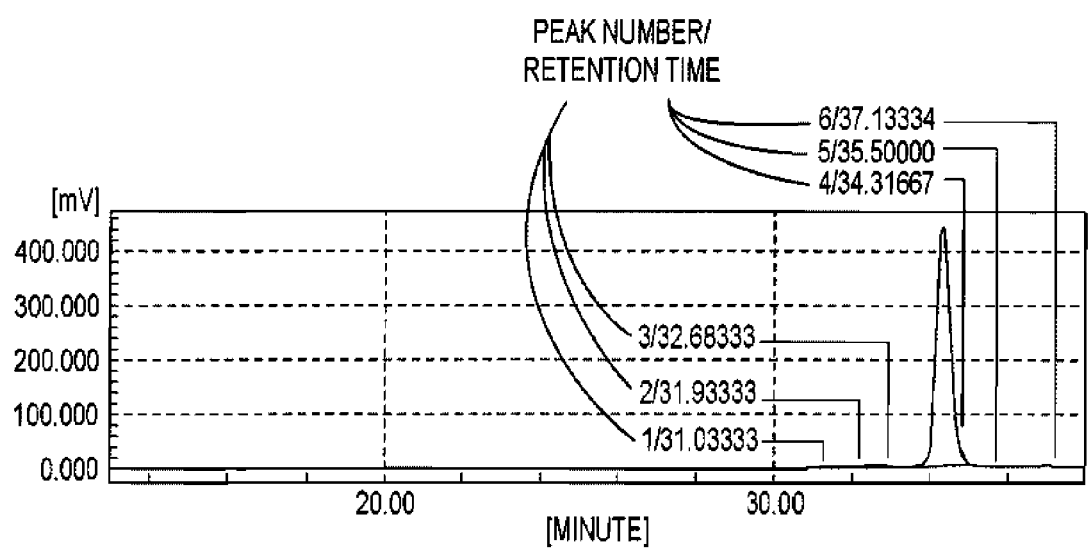
FIG. 5 is a diagram showing a GPC chart of the reaction product of Synthesis Example 1.

In a 1-L separable flask equipped with a stirrer, a reflux condenser, a dropping funnel and a thermometer, 31.4 g (0.33 mol) of 2-aminopyridine was placed, followed by charging of 150 g of tetrahydrofuran. The resultant mixture was stirred into a solution. Into the solution, 82.5 g (0.33 mol) of 3-isocyanatopropyltriethoxysilane was charged dropwise, and the thus-obtained mixture was stirred under heating at 70° C. for 4 hours. Subsequently, it is confirmed by IR measurement that an absorption peak attributable to the isocyanato group in the reactant 3-isocyanatopropyltriethoxysilane had disappeared completely and instead, an absorption peak attributable to a urea bond had been formed, the reaction was determined to be completed. The solvent was then distilled off to obtain the reaction product, which was a pale yellow liquid and had a viscosity of 184 mm²/s, a specific gravity of 1.094 and a refractive index of 1.4975. The reaction product was confirmed by GPC to be consisted of a single product, and was also confirmed by NMR spectroscopy to have a structure represented by the below-described chemical structural formula (8). A proton NMR spectrum of this compound is shown in FIG. 1, a carbon NMR spectrum in FIG. 2, a silicon NMR spectrum in FIG. 3, an IR spectrum in FIG. 4, and a GPC chart in FIG. 5.

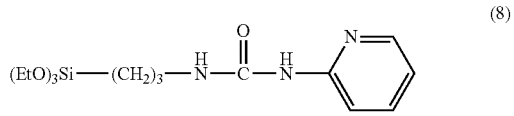

(8)

wherein Et represents an ethyl group, and this definition will apply equally hereinafter.

Synthesis Example 2

In a 1-L separable flask equipped with a stirrer, a reflux condenser, a dropping funnel and a thermometer, 31.7 g (0.33 mol) of 2-aminopyrimidine was placed, followed by charging of 150 g of tetrahydrofuran. The resultant mixture was stirred into a solution. Into the solution, 82.5 g (0.33 mol) of 3-isocyanatopropyltriethoxysilane was charged dropwise, and the thus-obtained mixture was stirred under heating at 70° C. for 4 hours. Subsequently, it is confirmed by IR measurement that an absorption peak attributable to the isocyanato group in the reactant 3-isocyanatopropyltriethoxysilane had disappeared completely and instead, an absorption peak attributable to a urea bond had been formed, the reaction was determined to be completed. The solvent was then distilled off to obtain the reaction product, which was an orange solid. The reaction product was confirmed by NMR spectroscopy to have the below-described chemical structural formula (9). Its NMR spectral data are as follows:

$^1$H-NMR (300 MHz, CDCl$_3$, δ(ppm)): 0.58 (t, 2H), 1.07 (t, 9H), 1.61 (quint, 2H), 3.28 (t, 2H), 3.67 (q, 6H), 6.66 (m, 1H), 6.88 (m, 1H), 7.39 (m, 1H), 7.97 (m, 1H), 9.34 (s, 1H), 10.01 (s, 1H).

$^{13}$C-NMR (75 MHz, CDCl$_3$, δ(ppm)): 7.6, 18.2, 23.2, 42.2, 58.0, 110.8, 113.7, 158.0, 163.2.

$^{29}$Si-NMR (60 MHz, CDCl$_3$, δ(ppm)): −45.7.

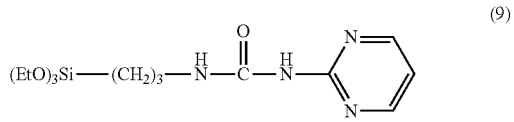

(9)

Synthesis Example 3

In a 1-L separable flask equipped with a stirrer, a reflux condenser, a dropping funnel and a thermometer, 89.4 g (0.75 mol) of 2-mercaptothiazoline and 1.3 g of dioctyltin oxide were placed, followed by charging of 300 g of ethyl acetate. The resultant mixture was stirred into a solution. Into the solution, 185.5 g (0.75 mol) of 3-isocyanatopropyltriethoxysilane was charged dropwise, and the thus-obtained mixture was stirred under heating at 80° C. for 4 hours. Subsequently, it is confirmed by IR measurement that an absorption peak attributable to the isocyanato group in the reactant 3-isocyanatopropyltriethoxysilane had disappeared completely and instead, an absorption peak attributable to a thiourethane bond had been formed, the reaction was determined to be completed. The solvent was then distilled off to obtain the reaction product, which was a pale yellow liquid and had a viscosity of 38 mm²/s, a specific gravity of 1.164 and a refractive index of 1.5218. The reaction product was confirmed by NMR spectroscopy to have the below-described chemical structural formula (10). Its NMR spectral data are as follows:

$^1$H-NMR (300 MHz, CDCl$_3$, δ(ppm)): 0.38 (t, 2H), 0.94 (t, 9H), 1.40 (quint, 2H), 3.02 (m, 2H), 3.04 (t, 2H), 3.54 (q, 6H), 4.42 (m, 2H), 9.52 (s, 1H).
$^{13}$C-NMR (75 MHz, CDCl$_3$, δ(ppm)): 7.2, 17.7, 22.2, 26.6, 42.5, 55.8, 57.8, 151.6, 199.6.
$^{29}$Si-NMR (60 MHz, CDCl$_3$, δ(ppm)): −45.7.

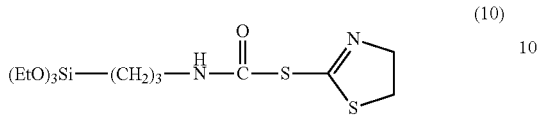

(10)

Synthesis Example 4

In a 1-L separable flask equipped with a stirrer, a reflux condenser, a dropping funnel and a thermometer, 33.4 g (0.33 mol) of 2-aminothiazole was placed, followed by charging of 150 g of tetrahydrofuran. The resultant mixture was stirred into a solution. Into the solution, 82.5 g (0.33 mol) of 3-isocyanatopropyltriethoxysilane was charged dropwise, and the thus-obtained mixture was stirred under heating at 80° C. for 4 hours. Subsequently, it is confirmed by IR measurement that an absorption peak attributable to the isocyanato group in the reactant 3-isocyanatopropyltriethoxysilane had disappeared completely and instead, an absorption peak attributable to a urea bond had been formed, the reaction was determined to be completed. The solvent was then distilled off to obtain the reaction product, which was a brown solid. The reaction product was confirmed by NMR spectroscopy to have the below-described chemical structural formula (11). Its NMR spectral data are as follows:

$^1$H-NMR (300 MHz, CDCl$_3$, δ(ppm)): 0.65 (t, 2H), 1.19 (t, 9H), 1.68 (quint, 2H), 3.32 (t, 2H), 3.69 (m, 1H), 3.79 (q, 6H), 6.26 (m, 2H), 7.28 (m, 2H).
$^{13}$C-NMR (75 MHz, CDCl$_3$, δ(ppm)): 7.7, 18.2, 23.4, 42.7, 58.3, 111.0, 136.8, 154.8, 162.6.
$^{29}$Si-NMR (60 MHz, CDCl$_3$, δ(ppm)): −45.8.

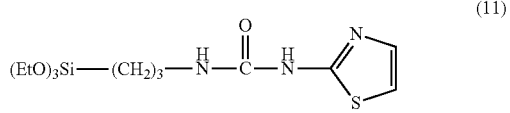

(11)

Synthesis Example 5

In a 1-L separable flask equipped with a stirrer, a reflux condenser, a dropping funnel and a thermometer, 50.1 g (0.33 mol) of 2-aminobenzothiazole was placed, followed by charging of 150 g of tetrahydrofuran. The resultant mixture was stirred into a solution. Into the solution, 82.5 g (0.33 mol) of 3-isocyanatopropyltriethoxysilane was charged dropwise, and the thus-obtained mixture was stirred under heating at 70° C. for 4 hours. Subsequently, it is confirmed by IR measurement that an absorption peak attributable to the isocyanato group in the reactant 3-isocyanatopropyltriethoxysilane had disappeared completely and instead, an absorption peak attributable to a urea bond had been formed, the reaction was determined to be completed. The solvent was then distilled off to obtain the reaction product, which was a white solid. The reaction product was confirmed by NMR spectroscopy to have the below-described chemical structural formula (12). Its NMR spectral data are as follows:

$^1$H-NMR (300 MHz, CDCl$_3$, δ(ppm)): 0.68 (t, 2H), 1.20 (t, 9H), 1.71 (quint, 2H), 3.35 (t, 2H), 3.53 (m, 1H), 3.72 (q, 1H), 3.81 (q, 6H), 7.21 (m, 1H), 7.35 (m, 1H), 7.68 (m, 2H).
$^{13}$C-NMR (75 MHz, CDCl$_3$, δ(ppm)): 7.4, 18.2, 23.2, 42.7, 58.4, 119.8, 121.1, 123.3, 126.0, 130.8, 149.0, 154.7, 161.7.
$^{29}$Si-NMR (60 MHz, CDCl$_3$, δ(ppm)): −45.9.

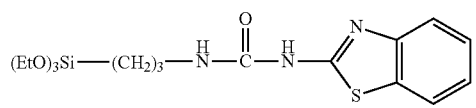

(12)

Synthesis Example 6

In a 1-L separable flask equipped with a stirrer, a reflux condenser, a dropping funnel and a thermometer, 57.5 g (0.5 mol) of N-hydroxysuccinimide and 1.0 g of dioctyltin oxide were placed, followed by charging of 300 g of tetrahydrofuran. The resultant mixture was stirred into a solution. Into the solution, 123.7 g (0.5 mol) of 3-isocyanatopropyltriethoxysilane was charged dropwise, and the thus-obtained mixture was stirred under heating at 70° C. for 4 hours. Subsequently, it is confirmed by IR measurement that an absorption peak attributable to the isocyanato group in the reactant 3-isocyanatopropyltriethoxysilane had disappeared completely and instead, an absorption peak attributable to a urethane bond had been formed, the reaction was determined to be completed. The solvent was then distilled off to obtain the reaction product, which was a pale yellow liquid and had a viscosity of 38 mm$^2$/s, a specific gravity of 1.164 and a refractive index of 1.5218. The reaction product was confirmed by NMR spectroscopy to have the below-described chemical structural formula (13). Its NMR spectral data are as follows:

$^1$H-NMR (300 MHz, CDCl$_3$, δ(ppm)): 0.35 (t, 2H), 0.94 (t, 9H), 1.38 (quint, 2H), 2.39 (m, 2H), 2.52 (m, 2H), 2.90 (t, 2H), 3.53 (q, 6H), 4.42 (m, 2H), 6.45 (m, 1H).
$^{13}$C-NMR (75 MHz, CDCl$_3$, δ(ppm)): 6.8, 17.6, 22.2, 24.8, 43.7, 57.7, 151.2, 170.2.
$^{29}$Si-NMR (60 MHz, CDCl$_3$, δ(ppm)): −45.4.

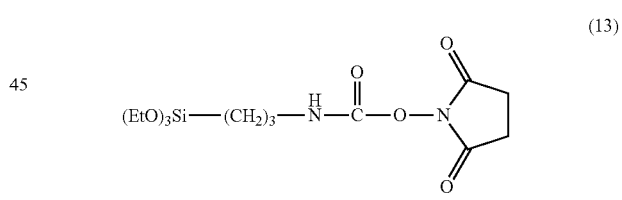

(13)

Synthesis Example 7

In a 1-L separable flask equipped with a stirrer, a reflux condenser, a dropping funnel and a thermometer, 48.9 g (0.3 mol) of N-hydroxyphthalimide and 1.0 g of dioctyltin oxide were placed, followed by charging of 200 g of ethyl acetate. The resultant mixture was stirred into a solution. Into the solution, 74.2 g (0.3 mol) of 3-isocyanatopropyltriethoxysilane was charged dropwise, and the thus-obtained mixture was stirred under heating at 80° C. for 4 hours. Subsequently, it is confirmed by IR measurement that an absorption peak attributable to the isocyanato group in the reactant 3-isocyanatopropyltriethoxysilane had disappeared completely and instead, an absorption peak attributable to a urethane bond had been formed, the reaction was determined to be completed. The solvent was then distilled off to obtain the reaction product, which was a yellow solid. The reaction product was confirmed by NMR spectroscopy to have the below-described chemical structural formula (14). Its NMR spectral data are as follows:

$^1$H-NMR (300 MHz, CDCl$_3$, δ(ppm)): 0.60 (t, 2H), 1.14 (t, 9H), 1.65 (quint, 2H), 3.20 (m, 2H), 3.75 (q, 6H), 6.30 (m, 1H), 7.72 (m, 4H).

$^{13}$C-NMR (75 MHz, CDCl$_3$, δ(ppm)): 7.3, 17.9, 22.6, 44.2, 58.3, 123.6, 128.7, 134.5, 152.2, 162.4.

$^{29}$Si-NMR (60 MHz, CDCl$_3$, δ(ppm)): −45.9.

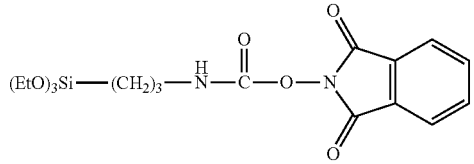

(14)

Synthesis Example 8

In a 1-L separable flask equipped with a stirrer, a reflux condenser, a dropping funnel and a thermometer, 53.2 g (0.3 mol) of N-hydroxymethylphthalimide and 1.0 g of dioctyltin oxide were placed, followed by charging of 200 g of ethyl acetate. The resultant mixture was stirred into a solution. Into the solution, 74.2 g (0.3 mol) of 3-isocyanatopropyltriethoxysilane was charged dropwise, and the thus-obtained mixture was stirred under heating at 80° C. for 4 hours. Subsequently, it is confirmed by IR measurement that an absorption peak attributable to the isocyanato group in the reactant 3-isocyanatopropyltriethoxysilane had disappeared completely and instead, an absorption peak attributable to a urethane bond had been formed, the reaction was determined to be completed. The solvent was then distilled off to obtain the reaction product, which was a white solid. The reaction product was confirmed by NMR spectroscopy to have the below-described chemical structural formula (15). Its NMR spectral data are as follows:

$^1$H-NMR (300 MHz, CDCl$_3$, δ(ppm)): 0.49 (t, 2H), 1.07 (t, 9H), 1.49 (quint, 2H), 3.04 (m, 2H), 3.68 (q, 6H), 5.39 (m, 1H), 5.55 (s, 2H), 7.69 (m, 4H).

$^{13}$C-NMR (75 MHz, CDCl$_3$, δ(ppm)): 7.3, 14.3, 17.9, 22.7, 43.1, 57.9, 123.2, 131.4, 134.1, 154.5, 166.4.

$^{29}$Si-NMR (60 MHz, CDCl$_3$, δ(ppm)): −45.6.

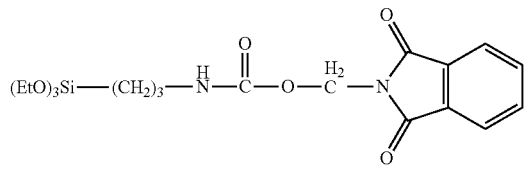

(15)

Synthesis Example 9

In a 1-L separable flask equipped with a stirrer, a reflux condenser, a dropping funnel and a thermometer, 98.1 g of n-butyl acrylate(BA), 0.6 g of acrylic acid(AA) and 1.3 g of 2-hydroxyethyl methacrylate(2-HEMA) were placed, followed by charging of 100 g of ethyl acetate as a solvent. The resultant mixture was stirred into a solution. Subsequently, nitrogen gas bubbling was conducted for 1 hour to remove oxygen so that the interior of the reaction system was purged with nitrogen, and the reaction system was maintained at 62° C. Into the reaction system, 0.03 g of azobisisobutyronitrile was charged as a polymerization initiator under stirring, followed by a reaction at 62° C. for 8 hours to obtain a (meth)acrylic copolymer as a base polymer.

Examples 1 to 8

With 100 parts by weight of the (meth)acrylic copolymer obtained in Synthesis Example 9, a trimethylolpropane-tolylene diisocyanate adduct (TDI) as a crosslinking agent and the silane coupling agent obtained in Synthesis Example 1 were mixed in accordance with the corresponding formula shown in Table 1 to obtain a pressure-sensitive adhesive composition. Using the silane coupling agents obtained in Synthesis Examples 2 to 8, pressure-sensitive adhesive compositions were likewise obtained in accordance with the corresponding formulas shown in Table 1, respectively.

The thus-obtained pressure-sensitive adhesive compositions were separately coated on release paper sheets, and were then dried to obtain uniform pressure-sensitive adhesive layers of 25 μm. The pressure-sensitive adhesive layers prepared as described above were bonded on iodine-based polarizers of 185 μm thickness, respectively. The thus-obtained polarizers were then cut into suitable sizes for use in various evaluations.

The thus-produced test pieces of the respective polarizers were evaluated for durability, glass adhesion properties, rework capability, and variations in adhesive force under high temperature or high temperature and high humidity conditions in accordance with the evaluation testing methods to be described subsequently herein. The evaluation results are shown in Tables 2 to 4.

Comparative Examples 1 to 3

Following a similar procedure and formulas as in the above-described examples except that the silane coupling agents B-1 to B-3 shown in Table 1 were used in place of the silane coupling agents of the present invention, pressure-sensitive adhesive compositions were produced, and a lamination processing step was conducted. With respect to the thus-obtained test pieces, similar evaluations were also performed as in the examples. The evaluation results are shown in Tables 2 to 4.

It is to be noted that the abbreviations in Table 1 have the following meanings:

n-BA: n-butyl acrylate

AA: acrylic acid

2-HEMA: 2-hydroxyethyl methacrylate

TDI: tolylene diisocyanate adduct of trimethylolpropane, crosslinking agent

Silane A-1: compound of Synthesis Example 1

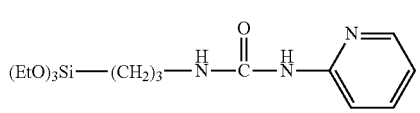

(8)

Silane A-2: compound of Synthesis Example 2

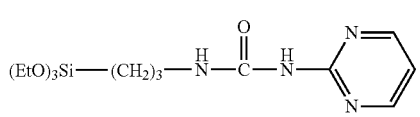

(9)

Silane A-3: compound of Synthesis Example 3

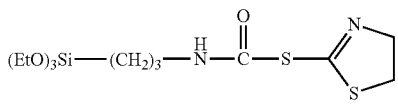
(10)

Silane A-4: compound of Synthesis Example 4

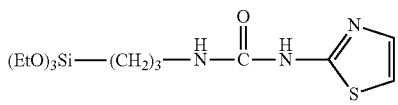
(11)

Silane A-5: compound of Synthesis Example 5

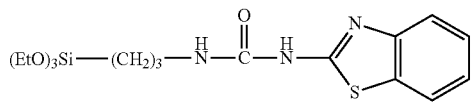
(12)

Silane A-6: compound of Synthesis Example 6

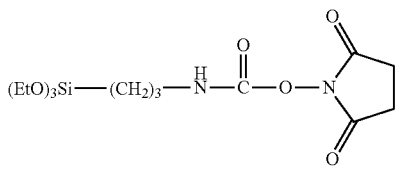
(13)

Silane A-7: compound of Synthesis Example 7

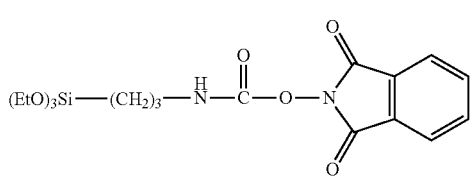
(14)

Silane A-8: compound of Synthesis Example 8

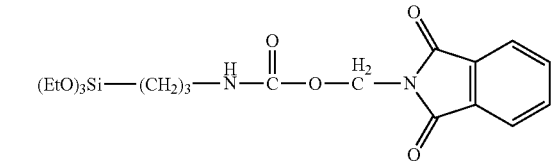
(15)

Silane B-1:

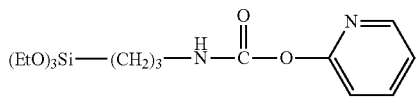

Silane B-2: γ-glycidoxypropyltrimethoxysilane ("KBM-403," product of Shin-Etsu Chemical Co., Ltd.)

Silane B-3: γ-isocyanatopropyltriethoxysilane ("KBE-9007," product of Shin-Etsu Chemical Co., Ltd.)

TABLE 1

| Parts by weight | | | Example | | | | | | | | Comparative Example | | |
|---|---|---|---|---|---|---|---|---|---|---|---|---|---|
| | | | 1 | 2 | 3 | 4 | 5 | 6 | 7 | 8 | 1 | 2 | 3 |
| Formula | Copolymer composition | n-BA | 98.1 | 98.1 | 98.1 | 98.1 | 98.1 | 98.1 | 98.1 | 98.1 | 98.1 | 98.1 | 98.1 |
| | | AA | 0.6 | 0.6 | 0.6 | 0.6 | 0.6 | 0.6 | 0.6 | 0.6 | 0.6 | 0.6 | 0.6 |
| | | 2-HEMA | 1.3 | 1.3 | 1.3 | 1.3 | 1.3 | 1.3 | 1.3 | 1.3 | 1.3 | 1.3 | 1.3 |
| | Crosslinking agent | TDI | 0.5 | 0.5 | 0.5 | 0.5 | 0.5 | 0.5 | 0.5 | 0.5 | 0.5 | 0.5 | 0.5 |
| | Silanes | A-1 | 1 | 0 | 0 | 0 | 0 | 0 | 0 | 0 | 0 | 0 | 0 |
| | | A-2 | 0 | 1 | 0 | 0 | 0 | 0 | 0 | 0 | 0 | 0 | 0 |
| | | A-3 | 0 | 0 | 1 | 0 | 0 | 0 | 0 | 0 | 0 | 0 | 0 |
| | | A-4 | 0 | 0 | 0 | 1 | 0 | 0 | 0 | 0 | 0 | 0 | 0 |
| | | A-5 | 0 | 0 | 0 | 0 | 1 | 0 | 0 | 0 | 0 | 0 | 0 |
| | | A-6 | 0 | 0 | 0 | 0 | 0 | 1 | 0 | 0 | 0 | 0 | 0 |
| | | A-7 | 0 | 0 | 0 | 0 | 0 | 0 | 1 | 0 | 0 | 0 | 0 |
| | | A-8 | 0 | 0 | 0 | 0 | 0 | 0 | 0 | 1 | 0 | 0 | 0 |
| | | B-1 | 0 | 0 | 0 | 0 | 0 | 0 | 0 | 0 | 1 | 0 | 0 |
| | | B-2 | 0 | 0 | 0 | 0 | 0 | 0 | 0 | 0 | 0 | 1 | 0 |
| | | B-3 | 0 | 0 | 0 | 0 | 0 | 0 | 0 | 0 | 0 | 0 | 1 |

Evaluation Tests
[Durability]

The durability of each polarizer was evaluated as will be described hereinafter. Two of the test pieces of the polarizer having the adhesive layer (90 mm×170 mm) were bonded on opposite sides of a glass substrate (110 m×190 mm×0.7 mm) in such a way that the optical absorption axes of the two test pieces cross over each other, whereby a laminate sample was prepared. The pressure applied upon bonding was approximately 5 kgf/cm², and the work was conducted in a clean room to avoid bubbles or dust particles. The above procedure was repeated to prepare other laminate samples.

To evaluate the moisture and heat resistance of those test pieces, the laminate samples were left over for 1,000 hours under the conditions of 60° C./90% RH, and then observed whether bubbles or separation had been developed. To evaluate the heat resistance of those test pieces, on the other hand, the laminate samples were left over for 1,000 hours under the conditions of 80° C./30% RH, and then observed for any bubbles or separation. It is to be noted that before the respective evaluations of the laminate samples, they were allowed to stand at room temperature (25° C.) for 24 hours. The results are shown in Table 2.

The following standards were employed for the evaluation of durability.

A: Neither bubbles nor separation occurred.
B: Bubbles and separation occurred slightly.
C: Bubbles and separation occurred significantly.

[Glass Adhesion Properties, and Variations in Adhesive Force Under High Temperature or High Temperature and High Humidity Conditions]

Glass adhesion properties and variations in adhesive force under high temperature or high temperature and high humidity conditions of each polarizer were evaluated as will be described hereinafter. After two of the test pieces of the polarizer having the adhesive layer were aged for 7 days at room temperature (23° C./60% RH), the test pieces were cut into equal sizes of 1 inch×6 inches. Using a 2-kg rubber roller, the test pieces were bonded onto alkali-free glass substrates of 0.7 mm thickness, respectively, to prepare laminate samples. Upon an elapsed time of 1 hour after being stored at room temperature, the laminate samples were measured for initial adhesive force. The laminate samples were then aged at 50° C. for 4 hours, and subsequent to storage at room temperature for 1 hour, its adhesive force was measured. The results are shown in Table 2.

To determine the degrees of increases in adhesive force under high temperature conditions and high temperature and high humidity conditions, laminate samples prepared by a similar procedure as described above were aged separately under conditions of 60° C./30% RH and conditions of 60° C./90% RH for respective times. Subsequent to the aging, each laminate sample was allowed to cool down at room temperature for 1 hour, and its adhesive force was then measured. The results are shown in Tables 3 and 4. For the measurement of the adhesive force, a tensile testing machine was used, and peeling strength was measured at a peeling rate of 300 mm/min and an angle of 180°.

[Rework Capability]

The rework capability of each polarizer was evaluated as will be described hereinafter. The test piece of the polarizer having the adhesive layer (90 mm×170 mm) was bonded on a glass substrate (110 mm×190 mm×0.7 mm) to prepare a laminate sample. After an elapsed time of 1 hour at room temperature initial bonding was measured, and the laminate sample was aged at 50° C. for 4 hours. After the laminate sample was allowed to cool down at room temperature for 1 hour, the test piece was peeled off from the glass substrate. The results are shown in Table 2.

The following standards were employed for the evaluation of rework capability.

A: Easy to separate.
B: A little hard to separate.
C: Impossible to separate, or glass substrate is broken.

The following Tables 2 to 4 summarize the evaluation results of the polarizers on which the pressure-sensitive adhesive compositions of the examples and comparative examples were applied, for durability, glass adhesion force, rework capability and variations in adhesive force under high temperature and under high temperature and high humidity as obtained in accordance with the above-described evaluation methods.

TABLE 2

| | | Glass adhesion force (gf/in) | | Durability/reliability | | |
|---|---|---|---|---|---|---|
| | | Initial adhesive force | 50° C. 4 hr | 60° C., 90% RH 1000 hr | 80° C., 30% RH 1000 hr | Rework capability |
| Example | 1 | 380 | 650 | A | A | A |
| | 2 | 390 | 780 | A | A | A |
| | 3 | 400 | 770 | A | A | A |
| | 4 | 390 | 810 | A | A | A |
| | 5 | 380 | 840 | A | A | A |
| | 6 | 430 | 820 | A | A | A |
| | 7 | 380 | 950 | A | A | A |
| | 8 | 370 | 880 | A | A | A |
| Comparative Example | 1 | 380 | 530 | A | B | A |
| | 2 | 1000 | 1500 | B | A | C |
| | 3 | 320 | 350 | B | B | C |

TABLE 3

Variations in glass adhesion force (gf/in) under high temperature

| Holding conditions | Example | | | | | | | | Comparative Example | | |
|---|---|---|---|---|---|---|---|---|---|---|---|
| 60° C., 30% RH | 1 | 2 | 3 | 4 | 5 | 6 | 7 | 8 | 1 | 2 | 3 |
| Initial | 380 | 390 | 400 | 390 | 380 | 430 | 380 | 370 | 380 | 1000 | 320 |
| 2 hours | 510 | 600 | 530 | 680 | 670 | 670 | 710 | 680 | 450 | 1300 | 380 |
| 6 hours | 650 | 780 | 770 | 810 | 840 | 820 | 950 | 880 | 490 | 1970 | 410 |
| 1 day | 810 | 900 | 870 | 920 | 950 | 920 | 1000 | 960 | 570 | 2000 | 530 |
| 3 days | 1300 | 1350 | 1340 | 1420 | 1400 | 1450 | 1580 | 1400 | 1060 | 2760 | 780 |
| 6 days | 2120 | 2200 | 2180 | 2290 | 2300 | 2380 | 2450 | 2400 | 1660 | 3870 | 800 |
| 10 days | 2700 | 2760 | 2810 | 2930 | 2950 | 3010 | 3100 | 2990 | 2240 | 4060 | 790 |

TABLE 3-continued

Variations in glass adhesion force (gf/in) under high temperature

| Holding conditions | Example | | | | | | | | Comparative Example | | |
|---|---|---|---|---|---|---|---|---|---|---|---|
| 60° C., 30% RH | 1 | 2 | 3 | 4 | 5 | 6 | 7 | 8 | 1 | 2 | 3 |
| 15 days | 3040 | 3110 | 3170 | 3290 | 3310 | 3360 | 3480 | 3450 | 2600 | 4120 | 850 |
| 20 days | 3040 | 3120 | 3190 | 3290 | 3330 | 3380 | 3510 | 3460 | 2650 | 4860 | 900 |

TABLE 4

Variations in glass adhesion force (gf/in) under high temperature and high humidity

| Holding conditions | Example | | | | | | | | Comparative Example | | |
|---|---|---|---|---|---|---|---|---|---|---|---|
| 60° C., 90% RH | 1 | 2 | 3 | 4 | 5 | 6 | 7 | 8 | 1 | 2 | 3 |
| Initial | 380 | 390 | 400 | 390 | 380 | 430 | 380 | 370 | 380 | 1000 | 320 |
| 2 hours | 500 | 580 | 550 | 620 | 600 | 630 | 700 | 600 | 430 | 1500 | 330 |
| 6 hours | 670 | 730 | 720 | 750 | 880 | 840 | 1000 | 810 | 500 | 2000 | 400 |
| 1 day | 860 | 920 | 870 | 920 | 1040 | 930 | 1050 | 920 | 650 | 2540 | 440 |
| 3 days | 1360 | 1410 | 1380 | 1450 | 1430 | 1480 | 1620 | 1430 | 1000 | 2670 | 450 |
| 6 days | 2110 | 2190 | 2150 | 2240 | 2280 | 2350 | 2430 | 2350 | 1630 | 4000 | 460 |
| 10 days | 2680 | 2730 | 2770 | 2880 | 2900 | 2990 | 3060 | 3000 | 2120 | 4250 | 560 |
| 15 days | 3030 | 3090 | 3140 | 3250 | 3200 | 3310 | 3410 | 3380 | 2200 | 4860 | 590 |
| 20 days | 3050 | 3100 | 3160 | 3250 | 3210 | 3330 | 3440 | 3390 | 2600 | 4960 | 480 |

The above-described results substantiate that the pressure-sensitive adhesive composition according to the present invention is excellent in initial rework capability, and after exposure to high temperature or high temperature and high humidity, can develop sufficient adhesive force of excellent long-term durability with glass.

Japanese Patent Application No. 2008-227777 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A pressure-sensitive adhesive composition comprising a organosilicon compound represented by the following formula (1):

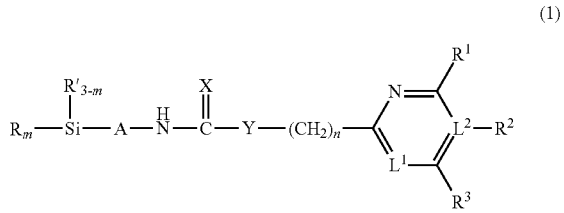

(1)

wherein R is a hydrolyzable group, R' is an alkyl group having 1 to 4 carbon atoms, A is a linear or branched alkylene group having 1 to 6 carbon atoms, x is an oxygen atom or sulfur atom, Y is —NH— or a sulfur atom, L1 and L2 are each independently a carbon atom or nitrogen atom, R1 to R3 are each independently a hydrogen atom, an alkyl, alkoxy or fluoroalkyl group having 1 to 6 carbon atoms, or an amino group, R1 and R2 or R2 and R3 may bond together to form a ring skeleton with the carbon atoms to which they are bonded and L2, m is an integer of 1 to 3, and n is an integer of 0 to 3.

2. The pressure-sensitive adhesive composition according to claim 1, comprising:
(A) 100 parts by weight of a (meth)acrylic copolymer obtainable by copolymerizing (a) 90 to 99.9 parts by weight of a (meth)acrylate ester monomer having an alkyl group having 1 to 12 carbon atoms and (b) 0.1 to 10 parts by weight of at least one of a vinyl monomer and (meth)acrylic monomer each of which contains a crosslinkable functional group,
(B) 0.01 to 10 parts by weight of a polyfunctional crosslinking agent, and
(C) 0.01 to 9 parts by weight of the organosilicon compound according to claim 1.

3. The pressure-sensitive adhesive composition according to claim 2, wherein at least one of the vinyl monomer and (meth)acrylic monomer (b) is selected from a group consisting of 2-hydroxyethyl(meth)acrylate, 3-hydroxypropyl(meth)acrylate, 4-hydroxybutyl(meth)acrylate, diethylene glycol mono(meth)acrylate, dipropylene glycol mono(meth)acrylate, (meth)acryloxypropyltrimethoxysilane, (meth)acryloxypropyltriethoxysilane, (meth)acryloxypropylmethyldimethoxysilane, (meth)acryloxypropylmethyldiethoxysilane, (meth)acryloxymethyltrimethoxysilane, (meth)acryloxymethyltriethoxysilane, (meth)acryloxymethylmethyldimethoxysilane, (meth)acryloxymethylmethyldiethoxysilane, (meth)acrylic acid, (meth)acrylic acid dimmer, itaconic acid, maleic acid, and maleic acid anhydride.

4. The pressure-sensitive adhesive composition according to claim 2, wherein the polyfunctional crosslinking agent (B) is at least one crosslinking agent selected from a group consisting of isocyanate compounds, epoxy compounds, aziridine compounds and metal chelate compounds.

5. The pressure-sensitive adhesive composition according to claim 1, which is cured into a product having a crosslink density of 5 to 95 wt %.

* * * * *